United States Patent [19]

Karanewsky

[11] Patent Number: 4,460,579

[45] Date of Patent: Jul. 17, 1984

[54] THIAZINE AND THIAZEPINE CONTAINING COMPOUNDS

[75] Inventor: Donald S. Karanewsky, East Windsor, N.J.

[73] Assignee: E. R. Squibb & Sons, Inc., Princeton, N.J.

[21] Appl. No.: 470,882

[22] Filed: Feb. 28, 1983

[51] Int. Cl.³ ............... A61K 31/675; C07D 279/06; C07D 281/04; C07D 281/10
[52] U.S. Cl. .................... 424/200; 424/202; 424/244; 424/246; 424/275; 544/54; 260/239.3 R; 260/239.3 B
[58] Field of Search ............ 260/239.3 R, 239.3 B; 544/54; 424/246, 275, 244, 200, 202

[56] References Cited

FOREIGN PATENT DOCUMENTS

| | | | |
|---|---|---|---|
| 46289 | 2/1982 | European Pat. Off. | 260/239.3 R |
| 46291 | 2/1982 | European Pat. Off. | 260/239.3 R |
| 46292 | 2/1982 | European Pat. Off. | 260/239.3 R |
| 58427 | 8/1982 | European Pat. Off. | 548/201 |
| 68173 | 1/1983 | European Pat. Off. | 260/239.3 R |

*Primary Examiner*—Robert T. Bond
*Attorney, Agent, or Firm*—Lawrence S. Levinson; Stephen B. Davis

[57] ABSTRACT

This invention is directed to compounds of the formula

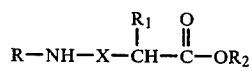

wherein X is a thiazine or thiazepine selected from

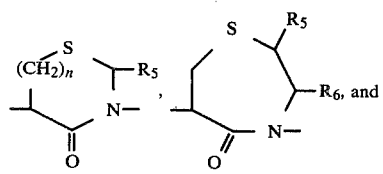

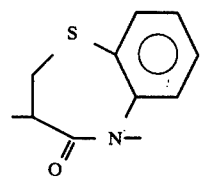

These compounds possess angiotensin converting enzyme inhibition activity and are thus useful as hypotensive agents.

18 Claims, No Drawings

THIAZINE AND THIAZEPINE CONTAINING COMPOUNDS

BACKGROUND OF THE INVENTION

Greenlee et al. in European Patent Application No. 58,427 disclose that phosphonamide derivatives of proline, pipecolic acid, and thiazolidinecarboxylic acid possess angiotensin converting enzyme inhibition activity.

Harris et al. in European Patent Application No. 46,289 disclose that various substituted enantholactam derivatives possess angiotensin converting enzyme inhibition activity.

Harris et al. in European Patent Application No. 46,291 disclose that various substituted caprolactam derivatives possess angiotensin converting enzyme inhibition activity.

Harris et al. in European Patent Application No. 46,292 disclose that various substituted caprylolactam derivatives possess angiotensin converting enzyme inhibition activity.

SUMMARY OF THE INVENTION

This invention is directed to the thiazine and thiazepine compounds of formula I and salts thereof

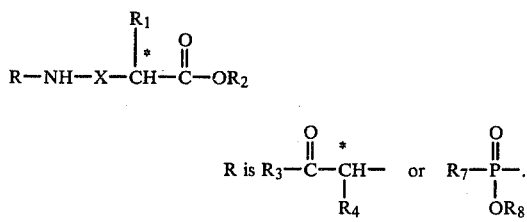

wherein $R_1$ is hydrogen, lower alkyl, amino substituted lower alkyl, hydroxy substituted lower alkyl, or halo substituted lower alkyl.

X is

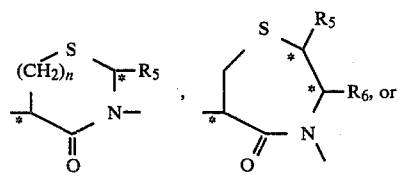

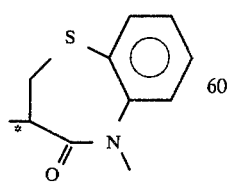

n is one or two.

$R_5$ and $R_6$ are independently selected from hydrogen, lower alkyl, —(CH$_2$)$_m$—cycloalkyl and

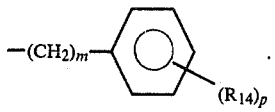

$R_3$ is hydroxy, lower alkoxy, di(lower alkyl)-amino-lower alkoxy, lower alkyl-carbonylamino-lower alkoxy, lower alkyl-carbonyloxy-lower alkoxy,

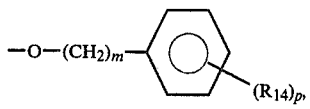

amino, lower alkyl-amino, di(lower alkyl)amino, hydroxy-amino, benzylamino, phenethylamino or —O—salt forming ion.

$R_4$ is hydrogen, lower alkyl,

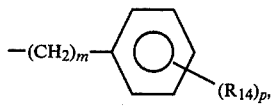

halo substituted lower alkyl, hydroxy substituted lower alkyl, —(CH$_2$)$_q$-cycloalkyl, —(CH$_2$)$_q$-carboxy, —(CH$_2$)$_q$—S-lower alkyl,

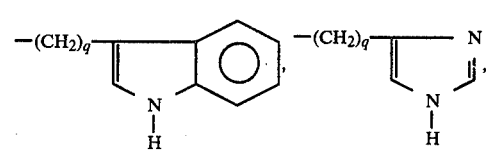

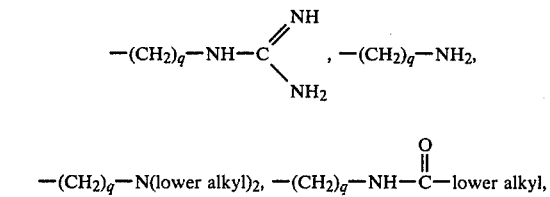

—(CH$_2$)$_q$—N(lower alkyl)$_2$, —(CH$_2$)$_q$—NH—C(O)—lower alkyl,

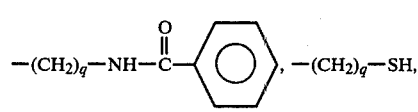

—(CH$_2$)$_q$—lower alkoxy, —(CH$_2$)$_q$—O—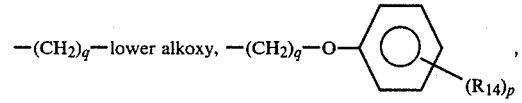,

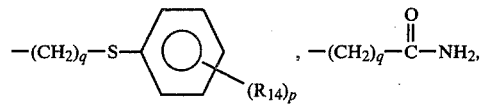

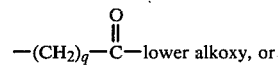

-continued

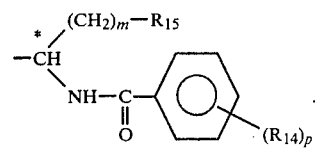

m is zero or an integer from 1 to 4.

q is an integer from 1 to 4.

$R_{14}$ is hydrogen, lower alkyl of 1 to 4 carbons, lower alkoxy of 1 to 4 carbons, lower alkylthio of 1 to 4 carbons, halo, trifluoromethyl, or hydroxy.

p is an integer from 1 to 3 provided that p is more than one only if $R_{14}$ is hydrogen, methyl, methoxy, chloro, or fluoro.

$R_{15}$ is lower alkyl, cycloalkyl, or

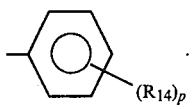

$R_7$ is alkyl of 1 to 10 carbons,

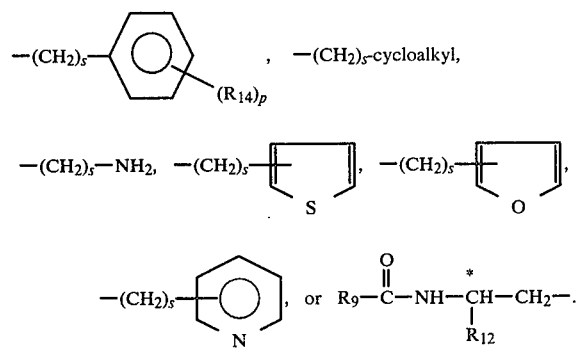

s is zero or an integer from 1 to 7.

t is an integer from 1 to 8.

$R_9$ and $R_{12}$ are independently selected from lower alkyl, halo substituted lower alkyl, —$(CH_2)_m$-cycloalkyl,

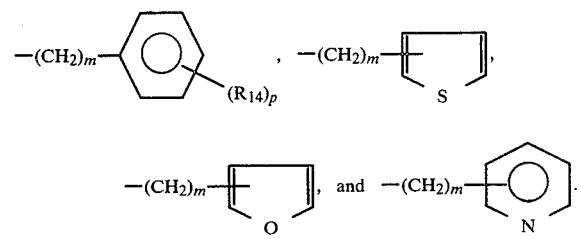

$R_8$ and $R_2$ are independently selected from hydrogen, lower alkyl, benzyl, benzhydryl, salt forming ion, and

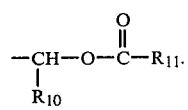

$R_{10}$ is hydrogen, lower alkyl, cycloalkyl, or phenyl.

$R_{11}$ is hydrogen, lower alkyl, lower alkoxy, cycloalkyl, phenyl, benzyl, or phenethyl.

DETAILED DESCRIPTION OF THE INVENTION

This invention in its broadest aspects relates to the thiazine and thiazepine compounds of formula I above, to compositions containing such compounds and to the method of using such compounds as anti-hypertensive agents.

The term alkyl used in defining $R_7$ refers to straight or branched chain hydrocarbon radicals having up to ten carbons, for example, methyl, ethyl, propyl, isopropyl, butyl, isobutyl, t-butyl, pentyl, isopentyl, heptyl, octyl, decyl, etc. The term lower alkyl used in defining various symbols refers to straight or branched chain radicals having up to seven carbons. The preferred lower alkyl groups are up to four carbons with methyl and ethyl most preferred. Similarly, the terms lower alkoxy and lower alkylthio refer to such lower alkyl groups attached to an oxygen or sulfur.

The term cycloalkyl refers to saturated rings of 3 to 7 carbon atoms with cyclopentyl and cyclohexyl being most preferred.

The term halogen refers to chloro, bromo, and fluoro.

The term halo substituted lower alkyl refers to such lower alkyl groups described above in which one or more hydrogens have been replaced by chloro, bromo, or fluoro groups such as trifluoromethyl, which is preferred, pentafluoroethyl, 2,2,2-trichloroethyl, choromethyl, bromomethyl, etc. Similarly, the terms amino substituted lower alkyl and hydroxy substituted lower alkyl refer to such lower alkyl groups described above in which one or more hydrogens have been replaced by —$NH_2$ or —OH, i.e., aminomethyl, 2-aminoethyl, 3-hydroxypropyl, etc.

The symbols

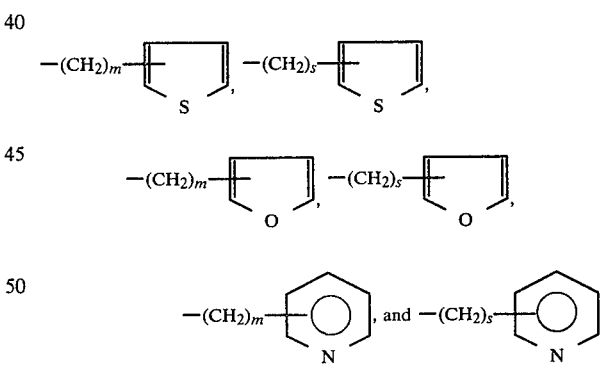

represent that the alkylene bridge is attached to an available carbon atom.

The compounds of formula I wherein

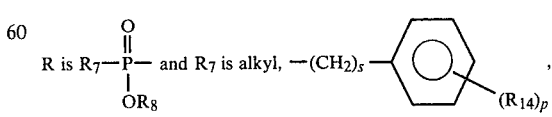

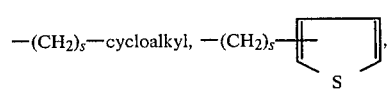

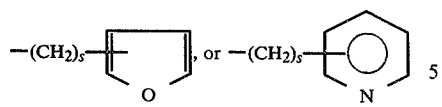

are prepared by coupling a phosphonochloridate of formula II wherein $R_8$ is lower alkyl, benzyl or benzhydryl

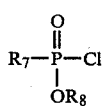

with the thiazine or thiazepine ester of the formula

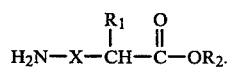

Preferably, the thiazine or thiazepine ester of formula III is in its hydrochloride salt form and $R_2$ is lower alkyl, benzyl or benzhydryl.

The products of formula I wherein either or both of $R_8$ and $R_2$ are lower alkyl, benzyl, or benzhydryl can be hydrogenated, for example, by treating with hydrogen in the presence of a palladium on carbon catalyst or chemically treated such as with sodium hydroxide in aqueous dioxane or with trimethylsilylbromide in dichloromethane to yield the products of formula I wherein $R_8$ and $R_2$ are hydrogen.

The ester products of formula I wherein $$R_2 \text{ is } -\underset{R_{10}}{\underset{|}{CH}}-O-\underset{}{\overset{O}{\underset{\|}{C}}}-R_{11}$$

may be obtained by employing the thiazine or thiazepine of formula III in the above reaction with the ester group already in place.

The ester products of formula I wherein $R_2$ is

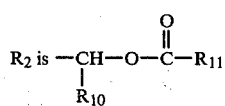

can also be obtained by treating the product of formula I wherein $R_2$ is hydrogen with a molar equivalent of the compound of the formula

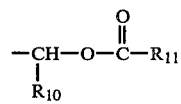

wherein L is a leaving group such as chlorine, bromine, tolylsulfonyloxy, etc. The diester products wherein $R_8$ and $R_2$ are the same and are

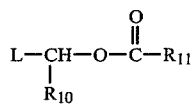

can be obtained by treating the product of formula I wherein $R_8$ and $R_2$ are both hydrogen or an alkali metal salt with two or more equivalents of the compound of formula IV.

The ester products of formula I wherein $R_8$ is

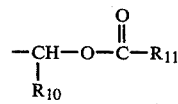

can be obtained by treating the product of formula I wherein $R_8$ is hydrogen or an alkali metal salt and $R_2$ is benzyl or benzhydryl with the compound of formula IV in the presence of base. Removal of the $R_2$ ester group such as by hydrogenation yields the products of formula I wherein $R_8$ is

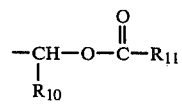

and $R_2$ is hydrogen.

The phosphonochloridates of formula II are described in the literature and in particular by Kosolapoff et al. in Organic Phosphorous Compounds, Vol. 7, Chapter 18 (Wiley, 1972).

The compounds of formula I wherein R is

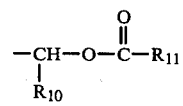

and $R_7$ is $-(CH_2)_r-NH_2$ are prepared by reacting a phthalidyl protected compound of the formula

wherein $R_8$ is lower alkyl, benzyl or benzhydryl with the thiazine ester of formula III, preferably wherein $R_2$ is benzyl, in the presence of triethylamine to yield the protected compound of the formula

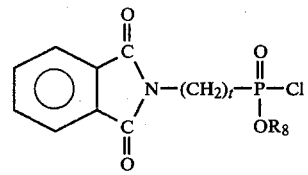

Treatment with hydrazine removes the phthalidyl protecting group after which the $R_8$ and $R_2$ ester group can be removed as described previously to yield the corresponding diacid compounds of formula I.

The phosphonochloridates of formula V can be prepared by treating a phthalidyl protected alkylbromide of the formula

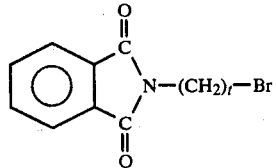 (VII)

with a trialkylphosphite of the formula

P(O-alkyl)$_3$ (VIII)

to yield the diester of the formula

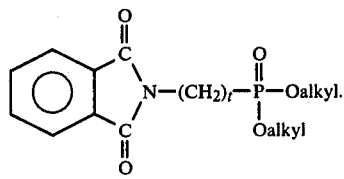 (IX)

Treatment of this diester with trimethylsilylbromide yields the phosphonic acid of the formula

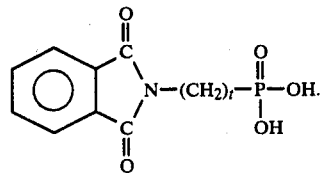 (X)

The acid of formula X can then be treated with phosphorous pentachloride and an alcohol of the formula

R$_8$—OH (XI)

in the presence of triethylamine to give the compound of formula V.

The compounds of formula I wherein R is

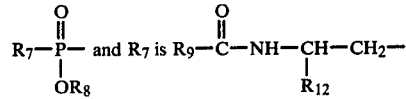

are prepared as follows. A protected amine of the formula

Ts—NH—CH(R$_{12}$)—CH$_2$—O—Ts (XII)

wherein Ts is tolylsulfonyl, i.e.,

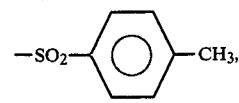

is reacted with sodium diethyl phosphonate, i.e.,

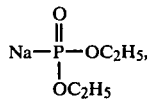

to yield the intermediate of the formula

Ts—NH—CH(R$_{12}$)—CH$_2$—P(O)(OC$_2$H$_5$)$_2$. (XIII)

Treatment with hydrogen bromide (48%) in the presence of phenol with heat yields the aminophosphonic acid of the formula

H$_2$N—CH(R$_{12}$)—CH$_2$—P(O)(OH)—OH. (XIV)

The aminophosphonic acid of formula XIV is then reacted with benzoyloxycarbonyl chloride or phthalic anhydride to yield Prot-NH—CH(R$_{12}$)—CH$_2$—P(O)(OH)—OH (XV)

wherein Prot is benzyloxycarbonyl or phthalidyl. The acid of formula XV is then converted to the phosphonochloridate of the formula Prot-NH—CH(R$_{12}$)—CH$_2$—P(O)(OR$_8$)—Cl (XVI)

wherein R$_8$ is lower alkyl, benzyl or benzhydryl by treating XV with triethylorthoformate, benzyl bromide, etc., followed by treatment with thionyl chloride or phosphorus pentachloride.

The acid chloride of formula XVI is then coupled with the thiazine or thiazepine ester of formula III to yield the intermediate of the formula

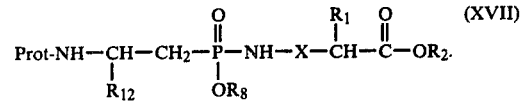 (XVII)

Removal of the protecting group such as by hydrogenation where Prot is benzyloxycarbonyl or by treatment with hydrazine where Prot is phthalidyl followed by reaction with the acid chloride of the formula R$_9$—C(O)—Cl (XVIII)

yields the desired products of formula I.

The thiazine or thiazepine ester of formula III wherein R$_5$ is other than hydrogen can be prepared as follows. A phthaloyl amino acid of the formula

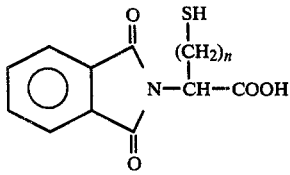  (XIX)

is reacted with an N-substituted glycine ester of the formula

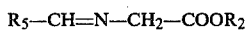  (XX)

in the presence of a coupling agent such as dicyclohexylcarbodiimide to yield the N-protected thiazine or thiazepine of the formula

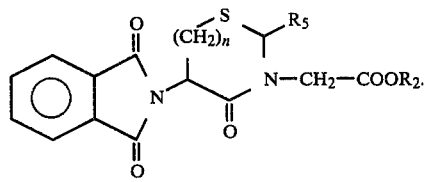  (XXI)

Treatment of the compound of formula XXI with methylhydrazine removes the phthalimido protecting group and yields the desired thiazine or thiazepine ester of formula III.

The N-protected thiazine or thiazepine of formula XXI can also be prepared by cyclizing a sulfoxide of the formula

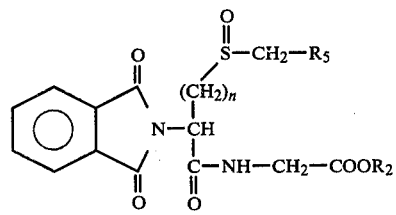  (XXII)

[prepared as set forth by Wolfe et al., Can. J. Chem., Vol. 57, p. 2412-2425 (1979)] by treatment with a mixture of trifluoroacetic acid anhydride and acetic anhydride followed by 2,6-lutidine.

The thiazine or thiazepine ester of formula III wherein $R_5$ is hydrogen can be prepared as follows. A dithiobis amino acid of the formula

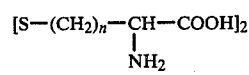  (XXIII)

is reacted with N-carboethoxyphthalimide to give the compound of the formula

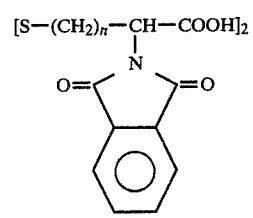  (XXIV)

which is treated with a glycine ester hydrochloride in the presence of base and a coupling agent such as carbonyldiimidazole to yield the compound of the formula

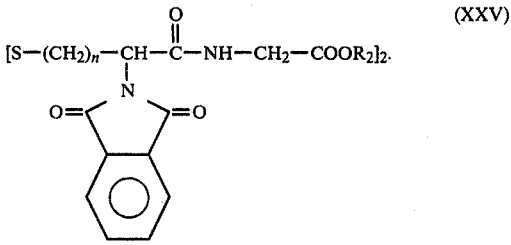  (XXV)

The dithiobis compound of formula XXV is treated with zinc dust to yield

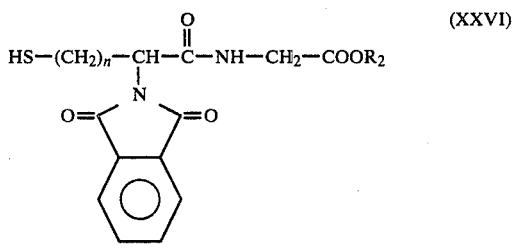  (XXVI)

which is then treated with bromomethyl methyl ether in the presence of pyridine to give

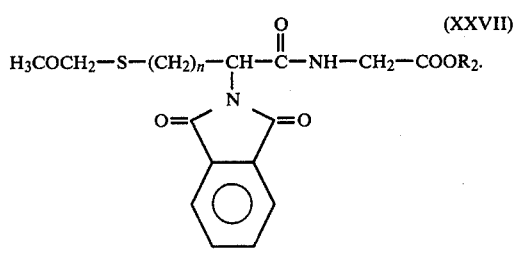  (XXVII)

The compound of formula XXVII is cyclized by treatment with camphorsulfonic acid to give the N-protected thiazine or thiazepine of the formula

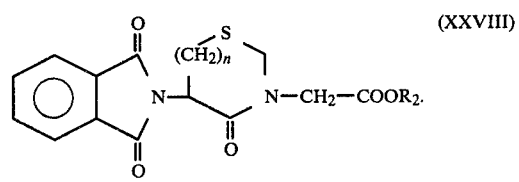  (XXVIII)

Treatment of the compound of formula XXVIII with methylhydrazine removes the phthalimido protecting group and yields the desired thiazine or thiazepine ester of formula III.

The thiazepine ester of formula III wherein X is

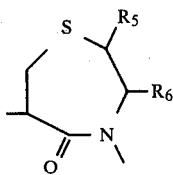

can be prepared as follows. An N-protected serine, for example, a t-butyloxycarbonyl N-protected serine, is treated with methyl iodide and cesium carbonate to yield the corresponding N-protected serine methyl ester. This methyl ester is then treated with diisopropylcarbodiimide and cuprous chloride to yield the N-protected dehydroalanine methyl ester of the formula

Treatment of the compound of formula XXIX with the aminothiol hydrochloride of the formula

in the presence of base yields the methyl ester of the formula

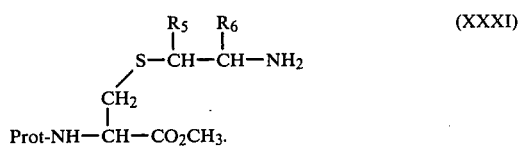

The compound of formula XXXI is converted to the carboxylic acid and then cyclized by treatment with diphenylphosphoryl azide to yield the compound of the formula

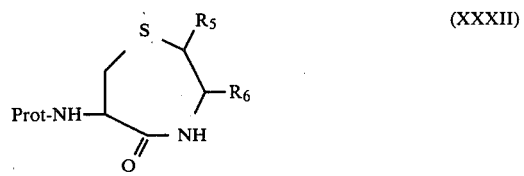

The thiazepine of formula XXXII is treated with a bromoacetate of the formula

to yield the compound

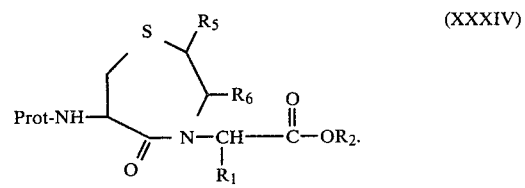

Removal of the protecting group, for example, by treating with hydrogen chloride in ethyl acetate when Prot is t-butyloxycarbonyl yields the desired thiazepine ester of formula III.

The thiazepine ester of formula III wherein X is

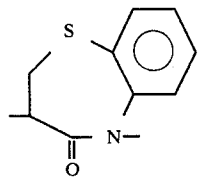

can be prepared as follows. The N-protected dehydroalanine methyl ester of formula XXIX is reacted with 2-aminothiophenol and 2,6-lutidine to give the compound of formula

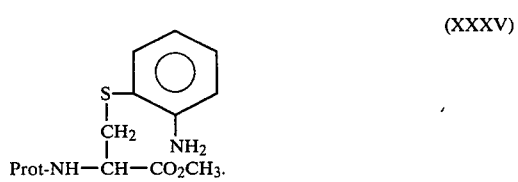

The methyl ester of formula XXXV is converted to the carboxylic acid and then cyclized by refluxing in xylene to give the compound of formula

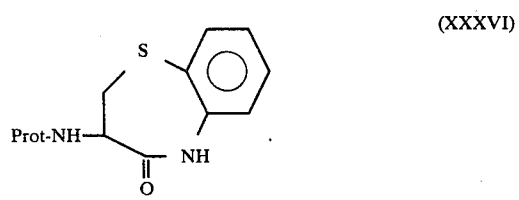

The thiazepine of formula XXXVI is treated with the bromoacetate of formula XXXIII and the N-protecting group is removed as described above to give the desired thiazepine ester.

The compounds of formula I wherein R is

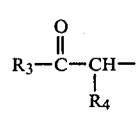

can be prepared as follows. A keto compound of the formula

is reacted with the thiazine or thiazepine of formula III in the presence of sodium cyanoborohydride to yield the ester of formula I.

If desired, the $R_2$ and $R_3$ ester groups can then be removed to yield the corresponding diacid compound.

The compounds of formula I wherein $R_3$ is lower alkoxy and $R_2$ is hydrogen can be prepared by converting the thiazine or thiazepine ester of formula III wherein $R_2$ is ethyl to the corresponding trimethylsilylethyl ester prior to reaction with the ketone of

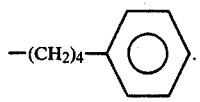

$R_1$ is hydrogen.

$R_5$ is hydrogen or phenyl.

$R_8$ and $R_2$ are independently selected from hydrogen, alkali metal salt, and

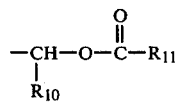

provided that only one of $R_2$ and $R_8$ is

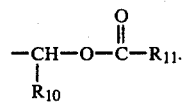

$R_{10}$ is hydrogen, straight or branched chain lower alkyl of 1 to 4 carbons, or cyclohexyl.

$R_{11}$ is straight or branched chain lower alkyl of 1 to 4 carbons.

The compounds of this invention wherein at least one of $R_8$ or $R_2$ is hydrogen or $R_3$ is hydroxy, form basic salts with various inorganic and organic bases which are also within the scope of the invention.

Such salts include ammonium salts, alkali metal salts like lithium, sodium and potassium salts (which are preferred), alkaline earth metal salts like calcium and magnesium salts, salts with organic bases, e.g., dicyclohexylamine salt, benzathine, N-methyl-D-glucamine, salts with amino acids like arginine, lysine and the like. The nontoxic, physiologically acceptable salts are preferred, although other salts are also useful, e.g., in isolating or purifying the product. The salts are formed using conventional techniques.

The symbol * is used to represent various asymmetric centers which may be present in the compounds of formula I. Thus, the compounds of this invention can accordingly exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods.

The compounds of formula I, and the physiologically acceptable salts thereof, are hypotensive agents. They inhibit the conversion of the decapeptide angiotensin I to angiotensin II and, therefore, are useful in reducing or relieving angiotensin related hypertension. The action of the enzyme renin or angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichlormethiazide, polythiazide or benzthiazide as well as ethacrynic acid, tricrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade. AG-50W-X8 refers to a crosslinked polystyrene-divinylbenzene sulfonic acid cation exchange resin. HP-20 refers to a porous crosslinked polystyrene-divinylbenzene polymer resin.

EXAMPLE 1

(R)-Dihydro-5-[[Hydroxy(4-phenylbutyl)phosphinyl]amino]-4-oxo-2-phenyl-2H-1,3-thiazine-3(4H)-acetic acid, dilithium salt (a) N-Phthaloyl-L-cysteine A solution of N,N'-diphthaloyl-L-cystine (19.5 g., 38.9 mmole) in a mixture of trifluoroacetic acid (60 ml.) and dry tetrahydrofuran (200 ml.) is cooled in an ice-bath under nitrogen and treated with zinc dust (15.3 g., 233.4 mmole) in three equal portions over a period of 15 minutes. The reaction is stirred cold for 2 hours, then filtered (celite) and concentrated in vacuo. The residue is partitioned between 600 ml. of ethyl acetate:ether (5:1) and a water-brine mixture. The organic layer is washed with water, brine and dried (MgSO$_4$). Removal of the solvents in vacuo yields 21.9 g. of crude product which is flash chromatographed on silica gel (400 g.) eluting with toluene:acetic acid (6:1). Fractions containing the desired product are combined to give 12.1 g. of N-phthaloyl-L-cysteine as an oil. $[\alpha]_D = -54.2°$ (c=1, formula II. The resulting product can then be treated to remove the $R_2$ trimethylsilylethyl ester group such as by use of tetrabutylammonium fluoride while leaving the $R_3$ ester group in place.

In the above reactions if $R_4$ is

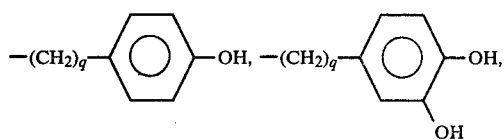

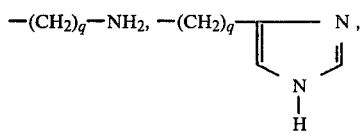

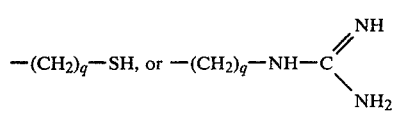

or if $R_1$ is amino or hydroxy substituted lower alkyl then the hydroxyl, amino, imidazolyl, mercaptan, or guanidinyl function should be protected during the coupling reaction. Suitable protecting groups include benzyloxycarbonyl, t-butoxycarbonyl, benzyl, benzhydryl, trityl, etc., and nitro in the case of quanidinyl. The protecting group is removed by hydrogenation, treatment with acid, or other known methods following completion of the reaction.

Preferred compounds of this invention are those of formula I wherein:

$R_3$ is hydroxy, lower alkoxy of 1 to 4 carbons, or —O-alkali metal salt.

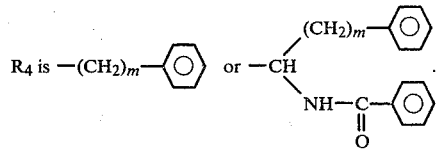

m is zero, one, two or three.
$R_7$ is alkyl of 1 to 10 carbons,

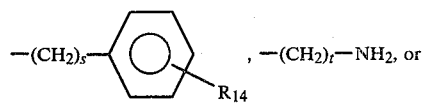

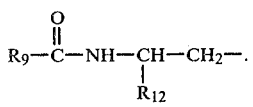

$R_9$ and $R_{12}$ are selected from lower alkyl of 1 to 4 carbons and

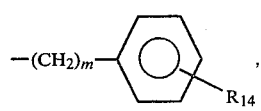

especially wherein $R_9$ is phenyl and $R_{12}$ is benzyl or phenethyl.

s is zero or an integer from 1 to 7.
t is an integer from 1 to 8.
$R_{14}$ is hydrogen, methyl, methoxy, methylthio, chloro, bromo, fluoro, or hydroxy.

$R_1$ is hydrogen, lower alkyl of 1 to 4 carbons, or —(CH$_2$)$_4$—NH$_2$.

$R_5$ and $R_6$ are independently selected from hydrogen, lower alkyl of 1 to 4 carbons, and

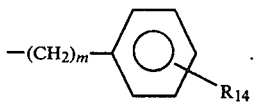

$R_8$ and $R_2$ are independently selected from hydrogen, lower alkyl of 1 to 4 carbons, alkali metal salt, or

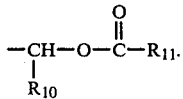

$R_{10}$ is hydrogen, straight or branched chain lower alkyl of 1 to 4 carbons, or cyclohexyl.

$R_{11}$ is straight or branched chain lower alkyl of 1 to 4 carbons, cyclohexyl or phenyl.

Most preferred compounds of this invention are those of formula I wherein:

X is

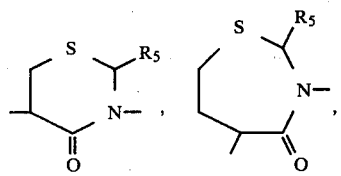

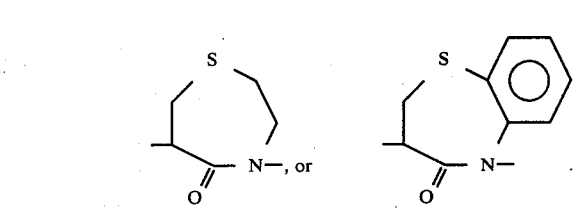

$R_3$ is hydroxy, ethoxy, or —O-alkali metal salt.
$R_4$ is

$R_7$ is alkyl of 1 to 10 carbons or

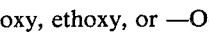

wherein s is zero or an integer from 1 to 7, especially methanol). TLC (toluene/acetic acid; 6:1) spot at $R_f=0.30$.

(b) N-Benzylideneglycine, ethyl ester

A mixture of glycine, ethyl ester, hydrochloride (10 g., 71.6 mmole), triethylamine (14.5 g., 143.2 mmole), and anhydrous $MgSO_4$ (6.0 g., 50.1 mmole) in dry methylene chloride (150 ml.) is treated with a solution of benzaldehyde (7.6 g., 71.6 mmole) in methylene chloride (10 ml.) added over a period of 15 minutes. After 5 hours, the reaction mixture is filtered, concentrated in vacuo, and then partitioned between 400 ml. of ether and 50 ml. of water. The organic layer is washed with water and brine, dried ($MgSO_4$), and concentrated in vacuo to give 12.1 g. of N-benzylideneglycine, ethyl ester.

(c) (R)-Dihydro-5-phthalimido-4-oxo-2-phenyl-2H-1,3-thiazine-3(4H)-acetic acid, ethyl ester To a solution of N-phthaloyl-L-cysteine (15.8 g., 62.8 mmole) and N-benzylideneglycine, ethyl ester (12.3 g., 64.3 mmole) in dry chloroform (160 ml.) cooled in an ice bath under nitrogen is added dicyclohexylcarbodiimide (13.0 g., 62.8 mmole) in one portion. After 2 hours, the cold reaction mixture is filtered, concentrated in vacuo and redissolved in a mixture of ether (500 ml.) and chloroform (200 ml). The organic extract is washed with saturated aqueous sodium bicarbonate, water, 5% potassium bisulfate and brine, dried ($MgSO_4$) and concentrated in vacuo to give 23.8 g. of crude product. Flash chromatography on silica (600 g.) eluting with hexane:ethyl acetate (3:1) yields 15.6 g. of (R)-dihydro-5-phthalimido-4-oxo-2-phenyl-2H-1,3-thiazine-3(4H) acetic acid, ethyl ester as a diastereomeric mixture.

(d) (R)-Dihydro-5-amino-4-oxo-2-phenyl-2H-1,3-thiazine-3(4H)-acetic acid, ethyl ester A mixture of (R)-dihydro-5-phthalimido-4-oxo-2-phenyl-2H-1,3-thiazine-3(4H)-acetic acid, ethyl ester (1.5 g., 3.5 mmole), methylhydrazine (0.3 ml., 1.6 eq.), and chloroform (10 ml.) is stirred at 25° in an argon atmosphere for 48 hours. The heterogeneous mixture is diluted with ethyl acetate, filtered, washed with water, brine, and evaporated. The residue is taken up into 5% potassium bisulfate and washed with ethyl acetate. The aqueous phase is made basic with saturated sodium bicarbonate, extracted with methylene chloride (twice), dried ($MgSO_4$), and evaporated to give 720 mg. of (R)-dihydro-5-amino-4-oxo-2-phenyl-2H-1,3-thiazine-3(4H)-acetic acid, ethyl ester as an oil. TLC (7:2:1, isopropanol/conc. $NH_4OH$/water) major spot at $R_f=0.77$.

(e) Chloro(4-phenylbutyl)phosphinic acid, ethyl ester

A mixture of 4-phenylbutyl chloride (8.0 g., 47.5 mmole) and triethylphosphite (15.0 ml., 72 mmole) is heated at reflux (bath temperature 185°) under argon for 41.5 hours. Distillation of the mixture gives 10.8 g. of diethyl (4-phenylbutyl)phosphonate as a colorless liquid; b.p. 152°-154° (1.0 mm of Hg.).

A mixture of diethyl (4-phenylbutyl)phosphonate (0.73 g., 2.6 mmole), benzene (10 ml.) and phosphorus pentachloride (1.0 eq.) is refluxed under argon for 30 minutes. The benzene and phosphorus oxychloride are removed in vacuo to give chloro(4-phenylbutyl)phosphinic acid, ethyl ester.

(f) (R)-Dihydro-5-[[ethoxy(4-phenylbutyl)phosphinyl]amino]-4-oxo-2-phenyl-2H-1,3-thiazine-3(4H)-acetic acid, ethyl ester A mixture of the crude chloro(4-phenylbutyl)phosphinic acid, ethyl ester (2.6 mmole), dry methylene chloride (9.0 ml.) and (R)-dihydro-5-amino-4-oxo-2-phenyl-2H-1,3-thiazine-3(4H)-acetic acid, ethyl ester (0.72 g., 2.4 mmole) at 0° (ice bath) in an argon atmosphere is treated dropwise with triethylamine (0.44 ml., 1.3 eq.) in methylene chloride (2 ml.) over 5 minutes. After 30 minutes, the ice bath is removed and the reaction mixture is stirred at room temperature for 16 hours. The mixture is diluted with ethyl acetate and washed successively with saturated sodium bicarbonate, 5% potassium bisulfate, brine, dried ($MgSO_4$), and evaporated. The residue (1.5 g.) is chromatographed on silica (80 g.) eluting with hexane/acetone (2:1) to give 1.0 g. of (R)-dihydro-5-[[ethoxy(4-phenylbutyl)phosphinyl]amino]-4-oxo-2-phenyl-2H-1,3-thiazine-3(4H)-acetic acid, ethyl ester as an oil after evaporation. TLC (hexane/acetone, 2:1) single spot at $R_f=0.5$.

(g) (R)-Dihydro-5-[[hydroxy(4-phenylbutyl)phosphinyl]amino]-4-oxo-2-phenyl-2H-1,3-thiazine-3(4H)-acetic acid, dilithium salt A mixture of the diethyl ester product from part (f) (1.0 g., 1.93 mmole), methylene chloride (4 ml.) and bromotrimethylsilane (0.5 ml., 2.0 eq.) is stirred at room temperature under argon for 16 hours. The methylene chloride and excess bromotrimethylsilane are removed in vacuo and the residue is taken up in acetonitrile (6 ml.) and 1N lithium hydroxide (6.0 ml., approximately 3.0 eq.). After 2 hours the acetonitrile is evaporated, the aqueous solution is filtered, and chromatographed on an HP-20 (200 ml.) column eluting with a linear gradient of water-acetonitrile (0→90% acetonitrile). The desired fractions are combined, evaporated to a small volume, filtered (millipore), and lyophilized to give 385 mg. of (R)-dihydro-5-[[(hydroxy(4-phenylbutyl)phosphinyl]amino]-4-oxo-2-phenyl-2H-1,3-thiazine-3(4H)-acetic acid, dilithium salt as a fluffy white solid. TLC (7:2:1 isopropanol/concentrated $NH_4OH$/water) isomers $R_f=0.66$, 0.62. $[\alpha]_D=-5.5$ (c=1.0,$H_2O$); m.p. 215° (decomp.).

Anal. Calcd. for $C_{22}H_{25}N_2O_5SPLi_2 \cdot 1.9H_2O$: C, 51.95; H, 5.71; N, 5.51; S, 6.30; P, 6.1 Found: C, 51.92; H, 5.32; N, 5.48; S, 6.40; P, 6.1.

EXAMPLE 2

5-[[Hydroxy(4-phenylbutyl)phosphinyl]amino]tetrahydro-4-oxo-1,3-thiazepine-3(2H)-acetic acid, dilithium salt (a) Bis(phthaloyl)homocystine A mixture of homocystine (5.36, 0.02 mole), soldium carbonate (4.24 g., 0.04 mole) and N-carboethoxyphthalimide (9.7 g., 0.044 mole) in water (50 ml.) is stirred for 4 hours, during which time it becomes homogeneous. The reaction mixture is washed with ethyl acetate, acidified with concentrated hydrochloric acid, and extracted with methylene chloride. The extracts are dried and evaporated to a residue which is chromatographed on silica gel eluting with methylene chloride/methanol- /acetic acid (40:1:1). The major fraction is crystallized from acetic acid, washed with water and dried to give 7.7 g. of bis(phthaloyl)homocystine as a white solid.

(b) bis(phthaloyl)homocystinylglycine, ethyl ester

A solution of bis(phthaloyl)homocystine (7.0 g., 0.013 mole) and carbonyldiimidazole (4.3 g., 0.026 mole) in tetrahydrofuran (40 ml.) is stirred for 1 hour at 0°, then treated with triethylamine (7.4 ml., 0.052 mole) and glycine, ethyl ester, hydrochloride (4.0 g., 0.026 mole). The mixture is stirred for 4 hours at room temperature, diluted with ethyl acetate, and washed with saturated sodium bicarbonate, 5% potassium bisulfate, and brine. The solution is dried ($MgSO_4$) and evaporated to a residue which is chromatographed on silica gel eluting with ethyl acetate/hexane (5:4). The major fraction (4.7 g.) is bis(phthaloyl)homocystinylglycine, ethyl ester.

(c) N-Phthaloyl-homocysteinylglycine, ethyl ester

A mixture of bis(phthaloyl)homocystinylglycine, ethyl ester (2.9 g., 0.041 mole) and acetic acid (8.2 ml.) in ethanol (40 ml.) is treated with zinc dust (1.62 g.) and stirred at room temperature for 1 hour. The mixture is filtered, the filtrate evaporated, and the residue taken up in ethyl acetate and washed with water and brine. The solution is evaporated to yield 2.9 g. of N-phthaloyl-homocysteinylglycine, ethyl ester as a yellow semi-solid.

(d) N-Phthaloyl-S-(methoxymethyl)homocysteinylglycine, ethyl ester

A solution of N-phthaloylhomocysteinylglycine, ethyl ester (0.97 g., 2.8 mmole) and pyridine (0.67 ml., 8.4 mmole) in methylene chloride (4 ml.) is added dropwise to bromomethyl methyl ether (0.56 ml., 7.0 mmole) in methylene chloride (1.5 ml.) at 0° under argon. The mixture is stirred for 2 hours at room temperature, then additional pyridine (0.67 ml., 8.4 mmole) and bromomethyl methyl ether (0.56 ml., 7.0 mmole) are added and the mixture is stirred 1.5 hours longer. The mixture is washed with water, 5% potassium bisulfate, dried ($MgSO_4$) and evaporated to yield a residue which is chromatographed on silica gel eluting with ethyl acetate/hexane (1:1) to give 0.78 g. of N-phthaloyl-S-(methoxymethyl)homocysteinylglycine, ethyl ester as an oil.

(e) 5-Phthalimido-tetrahydro-4-oxo-1,3-thiazepine-3(2H)-acetic acid, ethyl ester N-Phthaloyl-S-(methoxymethyl)homocysteinylglycine, ethyl ester (0.76 g., 2.0 mmole) and camphorsulfonic acid (0.01 g.) in benzene (15 ml.) are refluxed for 1 hour. Additional camphorsulfonic acid (0.05 g.) is added and reflux is continued for 2 more hours after which anhydrous p-toluenesulfonic acid (0.1 g.) is added and the mixture is refluxed for 20 hours. The mixture is then diluted with ethyl acetate and washed with saturated sodium bicarbonate, 5% potassium bisulfate, and brine, dried ($MgSO_4$) and evaporated. The residue is chromatographed on silica gel eluting with ethyl acetate to yield a main fraction which is then crystallized from toluene to give 0.51 g. of 5-phthalimido-tetrahydro-4-oxo-1,3-thiazepine-3(2H)-acetic acid, ethyl ester as a crystalline solid; m.p. 191.5°–193.5°.

(f) 5-Amino-tetrahydro-4-oxo-1,3-thiazepine-3(2H)-acetic acid, ethyl ester

A mixture of 5-phthalimido-tetrahydro-4-oxo-1,3-thiazepine-3(2H)-acetic acid, ethyl ester (0.48 g., 1.3 mmole) and methylhydrazine (0.12 ml.) in acetonitrile is stirred at room temperature for 3 days. The reaction mixture is diluted with ethyl acetate, filtered and evaporated to a residue which is taken up in 5% potassium bisulfate and washed with ethyl acetate. The aqueous phase is saturated with sodium bicarbonate and extracted with methylene chloride. The extracts are dried and evaporated to yield 0.2 g. of 5-amino-tetrahydro-4-oxo-1,3-thiazepine-3(2H)-acetic acid, ethyl ester as an oil. TLC (silica gel, 10% methanol in methylene chloride) $R_f=0.19$.

(g) 5-[[Ethoxy(4-phenylbutyl)phosphinyl]amino]tetrahydro-4-oxo-1,3-thiazepine-3(2H)-acetic acid, ethyl ester A mixture of crude chloro(4-phenylbutyl)phosphinic acid, ethyl ester, dry methylene chloride and 5-amino-tetrahydro-4-oxo-1,3-thiazepine-3(2H)-acetic acid, ethyl ester are reacted as set forth in Example 1(f). Work up of the reaction mixture according to Example 1(f) yields 5-[[ethoxy(4-phenylbutyl)phosphinyl]amino]tetrahydro-4-oxo-1,3-thiazepine-3(2H)-acetic acid, ethyl ester.

(h) 5-[[Hydroxy(4-phenylbutyl)phosphinyl]amino]tetrahydro-4-oxo-1,3-thiazepine-3(2H)-acetic acid, dilithium salt The diethyl ester product from part (g) is treated with bromotrimethylsilane according to the procedure of Example 1(g) and the residue is treated with 1N lithium hydroxide and worked up as set forth in Example 1(g) to give 5-[[hydroxy(4-phenylbutyl)phosphinyl]amino]-tetrahydro-4-oxo-1,3-thiazepine-3(2H)-acetic acid, dilithium salt.

EXAMPLES 3–16

Following the procedures of Examples 1 and 2, the thiazine or thiazepine shown below in Col. I is reacted with the phosphinic acid ester shown in Col. II to give the ester product shown in Col. III. The $R_2$ and $R_8$ ester groups can be removed to give the corresponding diacid which can then be converted to a salt or in the case of Examples 15 and 16 only the $R_8$ ester group would be removed. The $R_1$ protecting group shown in Examples 6 and 10 would be removed as the last step of the synthesis.

| | | | Col. I | | Col. II | Col. III | |
|---|---|---|---|---|---|---|---|
| Example | n | R5 | R1 | R2 | R7 | R7 | R8 |
| 3 | 1 | —H | —H | —C2H5 | | C6H5—(CH2)4— | —C2H5 |
| 4 | 2 | C6H5— | —CH3 | —C2H5 | | C6H5—(CH2)6— | —C2H5 |
| 5 | 1 | —CH3 | —H | —CH2—C6H5 | | C6H5—(CH2)2— | —CH2—C6H5 |
| 6 | 2 | —C2H5 | —(CH2)4NHCOCH2—C6H5 | —C2H5 | | H3C—(CH2)7— | —C2H5 |
| 7 | 1 | —CH2—C6H4—CH3 | —H | —C2H5 | | H3C—(CH2)3— | —C2H5 |
| 8 | 2 | —(CH2)2—C6H5 | —CF3 | —C2H5 | | (2-thienyl)—(CH2)4— | —C2H5 |
| 9 | 1 | —CH2—C6H11 | —C2H5 | —C2H5 | | (2-furyl)— | —C2H5 |
| 10 | 2 | cyclopentyl | —CH2OCH2—C6H5 | —C2H5 | | (2-pyridyl)—CH2— | —C2H5 |
| 11 | 1 | —C(CH3)3 | —H | —C2H5 | | 4-F—C6H4—CH2— | —C2H5 |
| 12 | 2 | —H | —H | —C2H5 | | 3,4-Cl2—C6H3—(CH2)2— | —C2H5 |
| 13 | 1 | —H | —H | —C2H5 | | 4-H3CO—C6H4—(CH2)4— | —C2H5 |
| 14 | 2 | —H | —H | —C2H5 | | C6H11—(CH2)4— | —C2H5 |
| 15 | 1 | —C6H5 | —H | —CH(C6H11)—O—C(O)—C2H5 | | C6H5—(CH2)4— | —C2H5 |
| 16 | 2 | —H | —H | —CH(CH(CH3)2)—O—C(O)—C2H5 | | C6H5—(CH2)4— | —C2H5 |

EXAMPLE 17

Tetrahydro-6-[[hydroxy(4-phenylbutyl)phosphinyl]amino]-5-oxo-1,4-thiazepine-4(5H)-acetic acid, dilithium salt (a) N-[(1,1-Dimethylethoxy)carbonyl]-L-serine, methyl ester To a solution of N-[(1,1-dimethylethoxy)carbonyl]-L-serine (20.5 g., 0.1 mole), methanol (50 ml.), and water (10 ml.) is added cesium carbonate (16.3 g., 0.5 eq.). After 5 minutes the solution becomes homogeneous, the methanol is stripped, and the residual water is removed azeotropically with acetonitrile (three times). The resulting foam is taken up in dry dimethylformamide (250 ml.) and treated with methyl iodide (6.2 ml., 10 eq.) at 25° under argon (slight exotherm). After 25 hours the reaction mixture is taken up in ethyl acetate and washed successively with saturated sodium bicarbonate, 5% potassium bisulfate, brine, dried (MgSO$_4$), and evaporated to give 17.5 g. of N-[(1,1-dimethylethoxy)carbonyl]-L-serine, methyl ester as a light green oil. TLC (ethyl acetate) single spot at R$_f$=0.71.

(b) 2-[[(1,1-Dimethylethoxy)carbonyl]amino]-2-propenoic acid, methyl ester

A mixture of N-[(1,1-dimethylethoxycarbonyl]-L-serine, methyl ester (18.4 g., 83.9 mmole), diisopropylcarbodiimide (14.4 ml., 1.1 eq.) and acetonitrile (30 ml.) is treated with cuprous chloride (2.6 g., 0.3 eq.) at 25° in an argon atmosphere. After stirring the green mixture for 16 hours, ethyl acetate is added and the resulting mixture is filtered (celite bed) and evaporated. The gelatinous residue (19.0 g.) is filtered through a pad of silica (100 g.) eluting with ethyl acetate/hexane (1:16) to give 8.2 g. of 2-[[(1,1-dimethylethoxy)carbonyl]amino]-2-propenoic acid, methyl ester as a light green liquid. TLC (ethyl acetate/hexane; 1:16) major spot at R$_f$=0.29.

(c) S-(2-Aminoethyl)-N-[(1,1-dimethylethoxy)carbonyl]-L-cysteine, methyl ester

A mixture of 2-aminoethanethiol, hydrochloride (5.5 g., 1.2 eq.), triethylamine (16.6 ml., 2.4 eq.), and methylene chloride (20 ml.) at 0° (ice bath) under argon is treated dropwise with 2-[[(1,1-dimethylethoxy)carbonyl]amino]-2-propenoic acid, methyl ester (8.2 g., 40.8 mmole) in methylene chloride (30 ml.) over a 15 minute period. The ice bath is then removed and the resulting solution is stirred for 20 hours. The reaction mixture is taken up in ethyl acetate, filtered, and washed successively with water (twice), saturated sodium bicarbonate, brine, and evaporated. The gelatinous residue (9.4 g.) is taken up in ether and added dropwise to a solution of oxalic acid (3.6 g.)/ethyl ether (250 ml.) to obtain the oxalate salt as a white solid after filtration. The oxalate salt is taken up in water and basified with saturated sodium bicarbonate. The resulting oil is extracted into methylene chloride (approximately 20 times) to give 7.5 g. of S-(2-aminoethyl)-N-[(1,1-dimethylethoxy)carbonyl]-L-cysteine, methyl ester as an oil after evaporation. TLC (methylene chloride/methanol/acetic acid; 8:1:1) major spot at R$_f$=0.52.

(d) (Hexahydro-5-oxo-1,4-thiazepin-6-yl)carbamic acid, (1,1-dimethylethyl)ester

A mixture of S-(2-aminoethyl)-N-[(1,1-dimethylethoxy)carbonyl]-L-cysteine, methyl ester (7.5 g., 26.9 mmole), 1N sodium hydroxide (31.0 ml., 1.15 eq.), and dioxane (30 ml.) is stirred at room temperature for 2 hours. The reaction is then treated with 1N hydrochloric acid (4.1 ml.) to quench excess hydroxide. The dioxane and water are evaporated and the residual water is removed azeotropically with acetonitrile (twice). The resulting foam is taken into dry dimethylformamide (100 ml.), treated with diphenylphosphoryl azide (6.5 ml., 1.1 eq.), and stirred under argon at 25° for 3.5 days. The reaction mixture is diluted with ethyl acetate and washed successively with water, saturated sodium bicarbonate, 5% potassium bisulfate, brine, dried (MgSO$_4$), and evaporated. The residue (3.0 g.) is taken up in hot ethyl acetate and upon cooling 1.1 g. of the product crystallizes as a colorless solid. The mother liquor (1.9 g.) is chromatographed on silica (70 g.) eluting with 5% acetone/methylene chloride to give an additional 0.4 g. of product as a slightly colored solid. A small portion of the product is recrystallized from toluene to give (hexahydro-5-oxo-1,4-thiazepin-6-yl)carbamic acid, (1,1-dimethylethyl) ester as fine colorless needles; m.p. 199.5°–201°. TLC (10% acetone/methylene chloride) single spot at R$_f$=0.49.

Anal. Calcd. for C$_{10}$H$_{18}$N$_2$O$_3$S: C, 48.76; H, 7.36; N, 11.37; S, 13.02. Found: C, 48.56; H, 7.09; N, 11.35; S, 13.01.

(e) 6-[[(1,1-Dimethylethoxy)carbonyl]amino]tetrahydro-5-oxo-1,4-thiazepine-4(5H)-acetic acid, ethyl ester A suspension of (hexahydro-5-oxo-1,4-thiazepin-6-yl)carbamic acid, (1,1-dimethylethyl)ester (1.35 g., 5.48 mmole) in dry tetrahydrofuran (10 ml.) under argon at 0° (ice bath) is treated with potassium tert-butoxide (0.68 g., 1.1 eq.) to effect an orange homogeneous solution. After 5 minutes, ethyl bromoacetate (1.1 ml., 1.8 eq.) is added, the ice bath removed, and the reaction mixture is stirred for 2 hours. The reaction mixture is then diluted with ethyl acetate and washed successively with saturated sodium bicarbonate, 5% potassium bisulfate, brine, dried (MgSO$_4$) and evaporated. The residue is chromatographed on silica (85 g.) eluting with 5% acetone/methylene chloride to give 1.65 g. of 6-[[(1,1-dimethylethoxy)carbonyl]amino]-tetrahydro-5-oxo-1,4-thiazepine-4(5H)-acetic acid, ethyl ester as an oil following evaporation. TLC (10% acetone/methylene chloride) single spot at R$_f$=0.71.

(f) 6-Amino-tetrahydro-5-oxo-1,4-thiazepine-4(5H)-acetic acid, ethyl ester, hydrochloride A mixture of 6-[[(1,1-dimethylethoxy)carbonyl]amino]-tetrahydro-5-oxo-1,4-thiazepine-4(5H)-acetic acid, ethyl ester (1.65 g., 4.96 mmole) and ethyl acetate (10 ml.) at 0° (ice bath) is treated with cold saturated hydrochloric acid/ethyl acetate (20 ml.). After stirring for 2 hours at 0°, nitrogen is passed through the solution to remove excess hydrochloric acid. The ethyl acetate is evaporated and the residue is triturated with ether (three times) to give 1.35 g. of 6-amino-tetrahydro-5-oxo-1,4-thiazepine-4(5H)-acetic acid, ethyl ester, hydrochloride as a yellow solid. TLC (methylene chloride/ methanol/acetic acid; 8:1:1) single spot at $R_f=0.5$ (visualized with ninhydrin and heat).

Anal. Calcd. for $C_9H_{16}N_2O_3S \cdot HCl \cdot 0.5H_2O$: C, 38.98; H, 6.52; N, 10.10; S, 11.56; Cl, 12.78. Found: C, 38.98; H, 6.73; N, 9.66; S, 11.32; Cl, 12.80.

(g)
Tetrahydro-6-[[ethoxy(4-phenylbutyl)phosphinyl]amino]-5-oxo-1,4-thiazepine-4(5H)-acetic acid, ethyl ester A mixture of crude chloro (4-phenylbutyl)phosphinic acid, ethyl ester (4.09 mmole), dry tetrahydrofuran (5 ml.), and 6-amino-tetrahydro-5-oxo-1,4-thiazepine-4(5H)-acetic acid, ethyl ester, hydrochloride (1.10 g., 4.09 mmole) at 0° (ice bath) in an argon atmosphere is treated dropwise with triethylamine (1.25 ml., 2.2 eq.) in tetrahydrofuran (5 ml.) over a 2 minute period. After 20 minutes the ice bath is removed, and the reaction mixture is stirred for an additional 2 hours. The reaction mixture is diluted with ethyl acetate and washed successively with saturated sodium bicarbonate, 5% potassium bisulfate, brine, dried ($MgSO_4$), and evaporated. The residue (2.0 g.) is chromatographed on silica (75 g.) eluting with 3:1 toluene/acetone to give 1.45 g. of tetrahydro-6-[[ethoxy(4-phenylbutyl)phosphinyl]amino]-5-oxo-1,4-thiazepine-4(5H)-acetic acid, ethyl ester as an oil. TLC (toluene/acetic acid; 3:1) single spot at $R_f=0.16$.

(h)
Tetrahydro-6-[[hydroxy(4-phenylbutyl)phosphinyl]amino]-5-oxo-1,4-thiazepine-4(5H)-acetic acid, dilithium salt A mixture of the diester product from part (g) (1.45 g., 3.17 mmole), methylene chloride (5 ml.), and bromotrimethylsilane (1.3 ml., 3.0 eq.) is stirred under argon at 25°. After 16 hours additional bromotrimethylsilane (1.0 eq.) is added. After an additional 3 hours the methylene chloride and excess bromotrimethylsilane are removed in vacuo and the residue is treated with dry acetonitrile (10 ml.) and 1N sodium hydroxide (10 ml., approximately 3 eq.). After 3 hours the acetonitrile is evaporated and the resulting aqueous phase is applied to an HP-20 (200 ml. bed) column eluting with a linear gradient water→acetonitrile (0/90%). The desired fractions are combined, evaporated to a small volume, and applied to an AG50W×8 ($Li^+$) (40 ml.) column eluting with water. The desired fractions are combined, filtered (millipore), and lyophilized to give 0.85 g. of tetrahydro-6-[[hydroxy(4-phenylbutyl)phosphinyl]amino]-5-oxo-1,4-thiazepine-4(5H)-acetic acid, dilithium salt as a white solid; m.p. darkens at 233°. TLC (isopropanol/conc. $NH_4OH$/water; 7:2:1) single spot at $R_f=0.71$.

Anal. Calcd. for $C_{17}H_{23}N_2O_5PSLi_2 \cdot 2.3H_2O$: C, 45.05; H, 6.12; N, 6.18; S, 7.07; P, 6.83. Found: C, 45.05; H, 5.77; N, 6.19; S, 6.92; P, 6.7.

EXAMPLES 18–28

Following the procedure of Example 17 but employing substituted 2-aminoethanethiol shown below in Col. I in part (c) one obtains the thiazepine shown below in Col. II. This thiazepine is then reacted with the phosphinic acid ester shown in Col. III to give the ester product shown in Col. IV. The $R_2$ and $R_8$ ester groups can be removed to give the corresponding diacid which can then be converted to a salt or in the case of Examples 27 and 28 only the $R_8$ ester group would be removed. The $R_1$ protecting group shown in Examples 24 and 25 would be removed as the last step of the synthesis.

Col. I $$HS-\underset{R_5}{\underset{|}{CH}}-\underset{R_6}{\underset{|}{CH}}-NH_2$$

Col. II (thiazepine structure with $H_2N$, S, $R_5$, $R_6$, $N-CH(R_1)-C(=O)-OR_2$)

Col. III $$R_7-\underset{OR_8}{\overset{O}{\underset{|}{\overset{||}{P}}}}-Cl$$

Col. IV (product structure with $R_7-P(=O)(OR_8)-NH-$ attached to thiazepine ring bearing $R_5$, $R_6$, and $N-CH(R_1)-C(=O)-OR_2$)

| Example | $R_5$ | $R_6$ | $R_1$ | $R_2$ | $R_7$ | $R_8$ |
|---------|-------|-------|-------|-------|-------|-------|
| 18 | —$CH_3$ | —H | —H | —$C_2H_5$ | $C_6H_5$—$(CH_2)_2$— | —$C_2H_5$ |
| 19 | —H | —$CH_3$ | —H | —$C_2H_5$ | $C_6H_5$—$(CH_2)_6$— | —$C_2H_5$ |
| 20 | —H | —H | —$CH_3$ | —$C_2H_5$ | $C_6H_5$— | —$C_2H_5$ |

-continued

Col. I $$\text{HS}-\underset{R_5}{\underset{|}{CH}}-\underset{R_6}{\underset{|}{CH}}-NH_2$$

Col. II

[Structure: thiazepine ring with $R_5$, $R_6$ substituents, $H_2N$, and N-CH($R_1$)-C(O)-OR$_2$ group]

Col. III $$R_7-\underset{\underset{OR_8}{|}}{\overset{\overset{O}{\|}}{P}}-Cl$$

Col. IV

[Structure: thiazepine ring with $R_5$, $R_6$, $R_7$-P(O)(OR$_8$)-NH, and N-CH($R_1$)-C(O)-OR$_2$ group]

| Example | $R_5$ | $R_6$ | $R_1$ | $R_2$ | $R_7$ | $R_8$ |
|---|---|---|---|---|---|---|
| 21 | –phenyl | –H | –H | –CH$_2$–phenyl | H$_3$C–(CH$_2$)$_5$– | –CH$_2$–phenyl |
| 22 | –H | –phenyl | –CH$_3$ | –C$_2$H$_5$ | 2-thienyl-CH$_2$– | –C$_2$H$_5$ |
| 23 | –CH$_3$ | –CH$_3$ | –H | –C$_2$H$_5$ | 4-pyridyl-(CH$_2$)$_4$– | –C$_2$H$_5$ |
| 24 | –CH$_2$–phenyl | –H | –(CH$_2$)$_4$NHCOCH$_2$–phenyl | –C$_2$H$_5$ | phenyl–(CH$_2$)$_4$– | –C$_2$H$_5$ |
| 25 | –H | –cyclohexyl | –(CH$_2$)$_2$OCH$_2$–phenyl | –C$_2$H$_5$ | 2-furyl-(CH$_2$)$_3$– | –C$_2$H$_5$ |
| 26 | –phenyl | –CH$_3$ | –H | –C$_2$H$_5$ | H$_3$C–phenyl–(CH$_2$)$_2$– | –C$_2$H$_5$ |
| 27 | –H | –H | –H | –CH(cyclohexyl)–O–C(O)–C$_2$H$_5$ | phenyl–(CH$_2$)$_4$– | –C$_2$H$_5$ |
| 28 | –phenyl | –H | –H | –CH(CH(CH$_3$)$_2$)–O–C(O)–C$_2$H$_5$ | phenyl–(CH$_2$)$_4$– | –C$_2$H$_5$ |

EXAMPLE 29

(±)-Dihydro-3-[[hydroxy(4-phenylbutyl)phosphinyl]amino]-4-oxo-1,5-benzothiazepine-5(2H)-acetic acid, dilithium salt (a) S-(2-Aminophenyl)-N-[(1,1-dimethylethoxy)carbonyl]-L-cysteine, methyl ester To a mixture of 2-amino-thiophenol (1.9 g., 15.4 mmole), methylene chloride (15 ml.), and 2,6-lutidine (1.8 ml., 1.0 eq.) at −20° (chloroform dry ice) is added 2-[[(1,1-dimethylethoxy)carbonyl]amino]-2-propenoic acid, methyl ester (3.0 g., 1.0 eq.) dropwise over 5 minutes. After one hour the cooling bath is removed and the reaction mixture is stirred for an additional 16 hours. The reaction mixture is diluted with ethyl acetate and washed with saturated sodium bicarbonate, water, brine, dried (MgSO$_4$), and evaporated. The residue (4.1 g.) is chromatographed on silica (125 g.) eluting with hexane/ethyl acetate (5:1) to give 2.5 g. of S-(2-aminophenyl)-N-[(1,1-dimethylethoxy)carbonyl]-L-cysteine, methyl ester as an oil after evaporation.

(b)
S-(2-Aminophenyl)-N-[(1,1-dimethylethoxy)carbonyl]-L-cysteine

A mixture of S-(2-aminophenyl)-N-[(1,1-dimethylethoxy)carbonyl]-L-cysteine, methyl ester (1.0 g., 3.1 mmole), 1N sodium hydroxide (3.1 ml., 1.0 eq.), and dioxane (6 ml.) is stirred at room temperature in an argon atmosphere for one hour. The reaction mixture is washed with ethyl acetate, neutralized with 1N hydrochloric acid (3.1 ml.) and extracted with methylene chloride (twice). The combined extracts are dried (MgSO$_4$) and evaporated to give 1.0 g. of S-(2-aminophenyl)-N-[(1,1-dimethylethoxy)carbonyl]-L-cysteine as a foam. TLC (methylene chloride/acetic acid/methanol; 100:5:5) major spot at R$_f$=0.5. The product crystallizes from xylene to give S-(2-aminophenyl)-N-[(1,1-dimethylethoxy)carbonyl]-L-cysteine as a fluffy crystalline solid; m.p. 109°–111°.

Anal. Calcd. for C$_{14}$H$_{20}$N$_2$O$_4$S: C, 53.83; H, 6.45; N, 8.97; S, 10.26. Found: C, 53.51; H, 6.28; N, 8.99; S, 10.26.

(c)
(±)-(2,3,4,5-Tetrahydro-4-oxo-1,5-benzothiazepin-3-yl)carbamic acid,1,1-dimethylethyl ester A suspension of S-(2-aminophenyl)-N-[(1,1-dimethylethoxy)carbonyl]-L-cysteine (0.65 g., 2.1 mmole) in xylene (15 ml.) is refluxed in a flask equipped with a Dean-Stark trap for 7 hours. Upon cooling of the reaction mixture the product crystallizes. The solid is collected by filtration, washed with xylene, and dried (high vacuum) to give 0.4 g. of (±)-(2,3,4,5-tetrahydro-4-oxo-1,5-benzothiazepin-3-yl)carbamic acid, 1,1-dimethylethyl ester as an off-white crystalline solid; m.p. 197°–200° (decomp.).

Anal. Calcd. for C$_{14}$H$_{18}$N$_2$O$_3$S: C, 57.12; H, 6.16; N, 9.52; S, 10.89. Found: C, 56.88; H, 6.17; N, 9.40; S, 10.87.

(d)
(±)-3-[[(1,1-Dimethylethoxy)carbonyl]amino]-3,4-dihydro-4-oxo-1,5-benzothiazepine-5(2H)-acetic acid, ethyl ester A mixture of (±)-(2,3,4,5-tetrahydro-4-oxo-1,5-benzothiazepin-3-yl)carbamic acid, 1,1-dimethylethyl ester (0.8 g., 2.7 mmole), tetrahydrofuran (10 ml.) and potassium tert-butoxide (0.4 g., 1.3 eq.) is stirred at 0° (ice bath) under argon for 10 minutes and then treated with ethyl bromoacetate (0.5 g., 1.7 eq.). After 3 minutes the ice bath is removed and the mixture is stirred for one hour. The reaction mixture is then diluted with ethyl acetate and washed successively with saturated sodium bicarbonate, 5% potassium bisulfate, and brine, dried (MgSO$_4$) and evaporated. The residue (1.3 g.) is chromatographed on silica (60 g.) eluting with hexane/ethyl acetate (4:1) to give 1.0 g. of (±)-3-[[(1,1-dimethylethoxy)carbonyl]amino]-3,4-dihydro-4-oxo-1,5-benzothiazepine-5(2H)-acetic acid, ethyl ester as a foam. TLC (hexane/ethyl acetate; 4:1) single spot at R$_f$=0.21.

(e)
(±)-3-Amino-3,4-dihydro-4-oxo-1,5-benzothiazepine-5(2H)-acetic acid, ethyl ester A mixture of (±)-3-[[(1,1-dimethylethoxy)carbonyl]amino]-3,4-dihydro-4-oxo-1,5-benzothiazepine-5(2H)-acetic acid, ethyl ester (1.0 g., 2.6 mmole), methylene chloride (5 ml.), and trifluoroacetic acid (3 ml.) is stirred under argon at 25° for 30 minutes. The methylene chloride and trifluoroacetic acid are removed in vacuo and the residue is taken up in ethyl acetate and the hydrochloride salt is precipitated with saturated hydrochloric acid/ethyl ether. The white solid is collected by filtration and washed with 2:1 ethyl acetate/ethyl ether to yield 0.7 g. of (±)-3-amino-3,4-dihydro-4-oxo-1,5-benzothiazepine-5(2H)-acetic acid, ethyl ester as a white solid; m.p. 231°–233° (decomp.). TLC (methylene chloride/acetic acid/methanol; 100:5:5) single spot at R$_f$=0.08.

Anal. Calcd. for C$_{13}$H$_{16}$N$_2$O$_3$S.HCl: C, 49.29; H, 5.41; N, 8.84; S, 10.12; Cl, 11.37. Found: C, 48.87; H, 5.31; N, 8.80; S, 10.05; Cl, 11.37.

(f)
(±)-Dihydro-3-[[ethoxy(4-phenylbutyl)phosphinyl]amino]-4-oxo-1,5-benzothiazepine-5(2H)-acetic acid, ethyl ester A mixture of crude chloro (4-phenylbutyl)phosphinic acid, ethyl ester (2.44 mmole), dry tetrahydrofuran (10 ml.), and (±)-3-amino-3,4-dihydro-4-oxo-1,5-benzothiazepine-5(2H)-acetic acid, ethyl ester (0.65 g., 2.05 mmole) at 0° (ice bath) in an argon atmosphere is treated dropwise with triethylamine (0.86 ml., 3.0 eq.) in tetrahydrofuran (5 ml.) over 1 minute. After standing at 0° for 20 minutes the ice bath is removed and the reaction mixture is stirred for 16 hours. The reaction mixture is diluted with ethyl acetate and washed successively with saturated sodium bicarbonate, 5% potassium bisulfate and brine, dried (MgSO$_4$), and evaporated. The residue (1.2 g.) is chromatographed on silica (60 g.) eluting with acetone/hexane (1:1) to give 0.8 g. of (±)-dihydro-3-[[ethoxy(4-phenylbutyl)phosphinyl]amino]-4-oxo-1,5-benzothiazepine-5(2H)-acetic acid, ethyl ester as an oil after evaporation. TLC (acetone/hexane; 2:1) two spots at R$_f$=0.59,0.65(isomers at phosphorus).

(g)
(±)-Dihydro-3-[[hydroxy(4-phenylbutyl)phosphinyl]amino]-4-oxo-1,5-benzothiazepine-5(2H)-acetic acid, dilithium salt A mixture of the diester product from part (f) (0.8 g., 1.59 mmole), dry methylene chloride (5 ml.), and bromotrimethylsilane (0.63 ml., 3.0 eq.) is stirred at room temperature in an argon atmosphere for 16 hours. The methylene chloride and bromotrimethylsilane are removed in vacuo and the residue is taken up in acetonitrile (approximately 5 ml.) and 1N lithium hydroxide (5.6 ml., 3.5 eq.) and stirred for 2 hours. The acetonitrile is stripped, the aqueous solution is filtered, and applied to an HP-20 (200 ml.) column eluting with a linear gradient water-acetonitrile (0→90% acetonitrile). The desired fractions are combined, filtered (millipore), and lyophilized to give 0.5 g. of (±)-dihydro-3-[[hydroxy(4-phenylbutyl)phosphinyl]amino]-4-oxo-1,5-benzothiazepine-5(2H)-acetic acid, dilithium salt as a fluffy white solid; m.p. 245° (decomp.).

TLC (isopropanol/conc. NH$_4$OH/water; 7:2:1)single spot at R$_f$=0.48.

Anal. Calcd. for C$_{21}$H$_{23}$N$_2$O$_5$SPLi$_2$.1.8H$_2$O: C, 51.19; H, 5.44; N, 5.68; S, 6.51; P, 6.3. Found: C, 51.24; H, 5.12; N, 5.53; S, 6.57; P, 6.2.

Similarly, by following the procedure of Example 29 but employing the various chloro (substituted) phosphinic acid esters shown in Col. II of Examples 3 to 16 and 18 to 28, other compounds within the scope of this invention are obtained.

EXAMPLE 30

(R)-Dihydro-5-[[(6-aminohexyl)hydroxyphosphinyl]amino]-4-oxo-2-phenyl-2H-1,3-thiazepine-3(4H)-acetic acid, dilithium salt

(a) N-(6-Bromohexyl)phthalimide

A mixture of crystalline 6-aminohexanol (11.7 g., 0.1 mole) and phthalic anhydride (14.8 g., 0.1 mole) is heated at 170° for 1.5 hours in an argon atmosphere. The evolved water is then removed with heat and argon flow. The reaction mixture is cooled to 100° and phosphorus tribromide (7.2 ml., 0.086 mole) is added in portions via gas tight syringe to the reaction mixture. A vigorous reaction occurs with each addition. After addition is complete, the reaction mixture is heated at 100° for an additional 30 minutes. The cooled reaction mixture is diluted with ethanol (20 ml.) then poured over ice-water and refrigerated overnight. A yellow solid is filtered and washed several times with cold water until the filtrate is nearly neutral. The crude solid is recrystallized from ethanol to give 21.0 g. of N-(6-bromohexyl)phthalimide as a pale yellow solid; m.p. 54°–55°. TLC (hexane-ethyl acetate; 1:1) shows a major spot at $R_f=0.8$.

(b) (6-Phthalimidohexyl)phosphonic acid, diethyl ester

A mixture of N-(6-bromohexyl)phthalimide (5.5 g., 17.7 mmole) and triethylphosphite (10.0 ml., 58.4 mmole) is refluxed (bath temperature 160°–165°) under argon for 16 hours. The volatiles are removed by distillation at 100° (bath temperature), 0.5 mm. of Hg to leave a pale yellow viscous oil. The crude product is purified by flash chromatography on silica gel (100 g.) eluting with acetone-hexane (1:2) to give 6.00 g. of (6-phthalimidohexyl)phosphonic acid, diethyl ester as a colorless viscous oil. TLC (acetone-hexane; 1:1) shows a single spot at $R_f=0.40$.

(c) Chloro(6-phthalimidohexyl)phosphinic acid, ethyl ester

A mixture of (6-phthalimidohexyl)phosphonic acid, diethyl ester, benzene, and phosphorus pentachloride is refluxed according to the procedure of Example 1(e) to give chloro(6-phthalimidohexyl) phosphinic acid, ethyl ester.

(d) (R)-Dihydro-5-[[ethoxy(6-phthalimidohexyl)phosphinyl]amino]-4-oxo-2-phenyl-2H-1,3-thiazine-3(4H)-acetic acid, ethyl ester Chloro(6-phthalimidohexyl)phosphinic acid, ethyl ester and (R)-dihydro-5-amino-4-oxo-2-phenyl-2H-1,3-thiazine-3(4H)-acetic acid, ethyl ester are reacted according to the procedure of Example 1(f) to give (R)-dihydro-5-[[ethoxy(6-phthalimidohexyl)phosphinyl]amino]-4-oxo-2-phenyl-2H-1,3-thiazine-3(4H)-acetic acid, ethyl ester.

(e) (R)-Dihydro-5-[[(6-aminohexyl)ethoxyphosphinyl]amino]-4-oxo-2-phenyl-2H-1,3-thiazine-3(4H)-acetic acid, ethyl ester A solution of (R)-dihydro-5-[[ethoxy(6-phthalimidohexyl)phosphinyl]amino]-4-oxo-2-phenyl-2H-1,3-thiazine-3(4H)-acetic acid, ethyl ester in dioxane is treated with hydrazine hydrate and stirred at room temperature under argon. After the reaction is completed, the mixture is diluted with toluene and the solvents decanted. The residue is triturated with methylene chloride and filtered. The combined filtrate is evaporated to dryness to give (R)-dihydro-5-[[(6-aminohexyl)ethoxyphosphinyl]amino]-4-oxo-2-phenyl-2H-1,3-thiazine-3(4H)-acetic acid, ethyl ester.

(f) (R)-Dihydro-5-[[(6-aminohexyl)hydroxyphosphinyl]amino]-4-oxo-2-phenyl-2H-1,3-thiazine-3(4H)-acetic acid, dilithium salt The diethyl ester product from part (e) is treated with bromotrimethylsilane in methylene chloride and the residue is taken up in acetonitrile and treated with 1N lithium hydroxide according to the procedure of Example 1(g) Work-up of the product according to the procedure of Example 1(g) gives (R)-dihydro-5-[[(6-aminohexyl)hydroxyphosphinyl]amino]-4-oxo-2-phenyl-2H-1,3-thiazine-3(4H)-acetic acid, dilithium salt.

EXAMPLES 31–34

Following the procedure of Example 30 but employing the aminoalcohol listed in Col. I one obtains the product listed in Col. II.

| Example | Col. I | Col. II |
| --- | --- | --- |
| 31 | 3-aminopropanol | (R)—Dihydro-5-[[(3-aminopropyl)hydroxyphosphinyl]amino]-4-oxo-2-phenyl-2H—1,3-thiazine-3(4H)—acetic acid, dilithium salt |
| 32 | 2-aminoethanol | (R)—Dihydro-5-[[(2-aminoethyl)hydroxyphosphinyl]amino]-4-oxo-2-phenyl-2H—1,3-thiazine-3(4H)—acetic acid, dilithium salt |
| 33 | 4-aminobutanol | (R)—Dihydro-5-[[(4-aminobutyl)hydroxyphosphinyl]amino]-4-oxo-2-phenyl-2H—1,3-thiazine-3(4H)—acetic acid, dilithium salt |
| 34 | 8-aminooctanol | (R)—Dihydro-5-[[(8-aminooctyl)hydroxyphosphinyl]amino]-4-oxo-2-phenyl-2H—1,3-thiazine-3(4H)—acetic acid, dilithium salt |

Similarly, by employing the thiazine or thiazepine esters of Examples 2 to 29 within the procedure of Examples 30 to 34, other compounds within the scope of the invention are obtained.

EXAMPLE 35

(R)-Dihydro-5-[[(2-(benzoylamino)-3-phenylpropyl]hydroxyphosphinyl]amino]-4-oxo-2-phenyl-2H-1,3-thiazine-3(4H)-acetic acid, dilithium salt

(a) 4-Methylbenzenesulfonic acid, 2-[[(4-methylphenyl)sulfonyl]amino]-3-phenylpropyl ester A solution of d,l-phenylalaninol, hydrochloride (9.4 g., 50.1 mmole) in dry pyridine (35 ml.) at 0° (ice bath) is treated with p-toluenesulfonyl chloride (19.4 g., 102 mmole) in small portions over a 15 minute period. The mixture is allowed to come to room temperature and stirred overnight. The mixture is evaporated to dryness and the residue partitioned between ethyl acetate and 5% potassium bisulfate. The ethyl acetate layer is washed successively with 5% potassium bisulfate, saturated sodium bicarbonate and saturated sodium chloride, dried (Na₂SO₄), and evaporated. The dark residue is filtered through a pad of silica gel eluting with methylene chloride then methylene chloride-ethyl acetate (1:1). Evaporation of the solvents and trituration of the residue with ether gives 13.93 g. of 4-methylbenzenesulfonic acid, 2-[[(4-methylphenyl)sulfonyl]amino]-3-phenylpropyl ester as white crystals; m.p. 95°–96°; TLC (ethyl acetate/hexane; 1:2) spot at $R_f=0.39$. A sample recrystallized from diisopropyl ether has m.p. 96°–98°.

(b) [2-[[(4-Methylphenyl)sulfonyl]amino]-3-phenylpropyl]-phosphonic acid, diethyl ester A solution of diethylphosphite (7.3 g., 52.9 mmole) in dry tetrahydrofuran (100 ml.) is treated with sodium hydride 50% oil dispersion (2.20 g., 45.8 mmole) in small portions under argon. The mixture is then refluxed for 30 minutes, cooled to room temperature, and treated with 4-methylbenzenesulfonic acid, 2-[[(4-methylphenyl)sulfonyl]amino]-3-phenylpropyl ester (6.9 g., 15 mmole). After 15 minutes, a white solid separates; additional tetrahydrofuran (75 ml.) is added and stirring continued overnight. After stirring at room temperature overnight, the mixture is refluxed for one hour, cooled and partitioned between ethyl acetate (75 ml.) and 5% potassium bisulfate (50 ml.). The ethyl acetate phase is washed successively with 5% potassium bisulfate, saturated sodium bicarbonate and saturated sodium chloride, dried (Na₂SO₄), and evaporated. The residue is triturated with hexane to give 5.9 g. of [2-[[(4-methylphenyl)sulfonyl]amino]-3-phenylpropyl]phosphonic acid, diethyl ester as an off-white solid; m.p. 86°–89°; TLC (ethyl acetate) spot at $R_f=0.48$. A sample recrystallized from diisopropyl ether has m.p. 94°–95°.

(c) (2-Amino-3-phenylpropyl)phosphinic acid

A mixture of [2-[[(4-methylphenyl)sulfonyl]amino]-3-phenylpropyl]phosphonic acid, diethyl ester (5.9 g., 13.9 mmole), phenol (8.0 g., 85.1 mmole), and 48% aqueous hydrobromic acid (50 ml.) is refluxed for 5.5 hours. The cooled mixture is diluted with water (50 ml.) and washed with ethyl acetate (2×50 ml.). The aqueous phase is evaporated to dryness, taken up in water (30 ml.) and evaporated again. This is repeated twice more. Finally, the residue is taken up in water and applied to an AG 50 W-X2 (H+ form) column (60 ml. bed volume) and eluted first with water then with 5% pyridine-water. The fractions containing the desired product are combined and evaporated to dryness. The solid residue is triturated with acetonitrile to give 2.55 g. of (2-amino-3-phenylpropyl)phosphinic acid as an off-white crystalline solid; m.p. 347° (dec.); TLC (isopropanol/conc. NH₄OH/water; 7:2:1) spot at $R_f=0.27$.

(d) (2-Phthalimido-3-phenylpropyl)phosphinic acid

A mixture of (2-amino-3-phenylpropyl)phosphinic acid (2.0 g., 9.3 mmole) and phthalic anhydride (1.55 g., 10.5 mmole) is fused in a flask under argon at 195°–200° (bath temperature) for 1.5 hours. The glassy dark residue is refluxed with ethyl acetate (25 ml.) until the glassy residue dissolves and a fluffy crystalline solid separates. The cooled mixture is diluted with diethyl ether (25 ml.) and filtered. The solid is washed thoroughly with diethyl ether and dried to give 2.87 g. of (2-phthalimido-3-phenylpropyl)phosphinic acid as an off-white crystalline solid; m.p. 127°–130°. A sample recrystallized from ethyl acetate m.p. 129°–131°; TLC (isopropanol/conc. NH₄OH/water; 7:2:1) spot at $R_f=0.33$.

(e) (R)-Dihydro-5-[[[2-phthalimido-3-phenylpropyl]ethoxyphosphinyl]amino]-4-oxo-2-phenyl-2H-1,3-thiazine-3(4H)-acetic acid, ethyl ester A suspension of (2-phthalimido-3-phenylpropyl)-phosphinic acid in dry benzene is treated with phosphorus pentachloride and stirred at room temperature under argon for an hour. The mixture is then refluxed for 15 minutes, cooled and evaporated to dryness at room temperature (0.5 mm. of Hg). The residue is taken up in dry methylene chloride and reacted successively with a mixture of ethanol (1 eq.) and triethylamine (1 eq.) in methylene chloride and (R)-dihydro-5-amino-4-oxo-2-phenyl-2H-1,3-thiazine-3(4H)-acetic acid, ethyl ester in the presence of triethylamine according to the procedure of Example 1(f). Work up of the reaction mixture according to the procedure of Example 1(f) yields (R)-dihydro-5-[[[2-phthalimido-3-phenylpropyl]ethoxyphosphinyl]amino]-4-oxo-2-phenyl-2H-1,3-thiazine-3(4H)-acetic acid, ethyl ester.

(f) (R)-Dihydro-5-[[[2-(benzoylamino)-3-phenylpropyl]ethoxyphosphinyl]amino]-4-oxo-3-phenyl-2H-1,3-thiazine-3(4H)-acetic acid, ethyl ester A solution of (R)-dihydro-5-[[[2-phthalimido-3-phenylpropyl]ethoxyphosphinyl]amino]-4-oxo-2-phenyl-2H-1,3-thiazine-3(4H)-acetic acid, ethyl ester in dioxane is treated with hydrazine hydrate and stirred for 24 hours at room temperature. The mixture is then partitioned between ethyl acetate-water and the ethyl acetate phase was washed with water and saturated sodium chloride, dried (Na₂SO₄), and evaporated. The residue is taken up in dry toluene and refluxed for one hour. The mixture is filtered, treated with triethylamine and benzoyl chloride and stirred at room temperature for 30 minutes. The mixture is diluted with ethyl acetate, washed successively with 5% potassium bisulfate, saturated sodium bicarbonate, and saturated sodium chloride, dried (Na₂SO₄), and evaporated. The residue is chromatographed on silica gel to give (R)-dihydro-5-[[[2-(benzoylamino)-3-phenylpropyl]ethoxyphosphinyl]amino]-4-oxo-2-phenyl-2H-1,3-thiazine-3(4H)-acetic acid, ethyl ester.

(g) (R)-Dihydro-5-[[[2-(benzoylamino)-3-phenylpropyl]hydroxyphosphinyl]amino]-4-oxo-2-phenyl-2H-1,3-thiazine-3(4H)-acetic acid, dilithium salt The diethyl ester product from part (f) is treated with bromotrimethylsilane in methylene chloride and the residue is taken up in acetonitrile and treated with 1N lithium hydroxide according to the procedure of Example 1(g). Work up of the product according to the procedure of Example 1(g) gives (R)-dihydro-5-[[[2-(benzoylamino)-3-phenylpropyl]hydroxyphosphinyl]amino]-4-oxo-2-phenyl-2H-1,3-thiazine-3(4H)-acetic acid, dilithium salt.

EXAMPLES 36–45

Following the procedure of Example 35 but employing the protected amine shown in Col. I and the phosphinic diester shown in Col. II, one obtains, after removal of the tosyl protecting group and reaction with phthalic anhydride, the phosphinic acid shown in Col. III. The acid of Col. III is then converted to the phosphinic acid ester chloride shown in Col. IV which is then coupled with the thiazine ester shown in Col. V to yield the intermediate shown in Col. VI. Removal of the phthalidyl group and reaction with the acid chloride shown in Col. VII yields the ester product shown in Col. VIII. The $R_2$ and $R_8$ ester groups can be removed to give the corresponding diacid which can then be converted to a salt or in the case of Example 45 only the $R_8$ ester group would be removed. The $R_1$ protecting group shown in Example 40 would be removed as the last step of the synthesis.

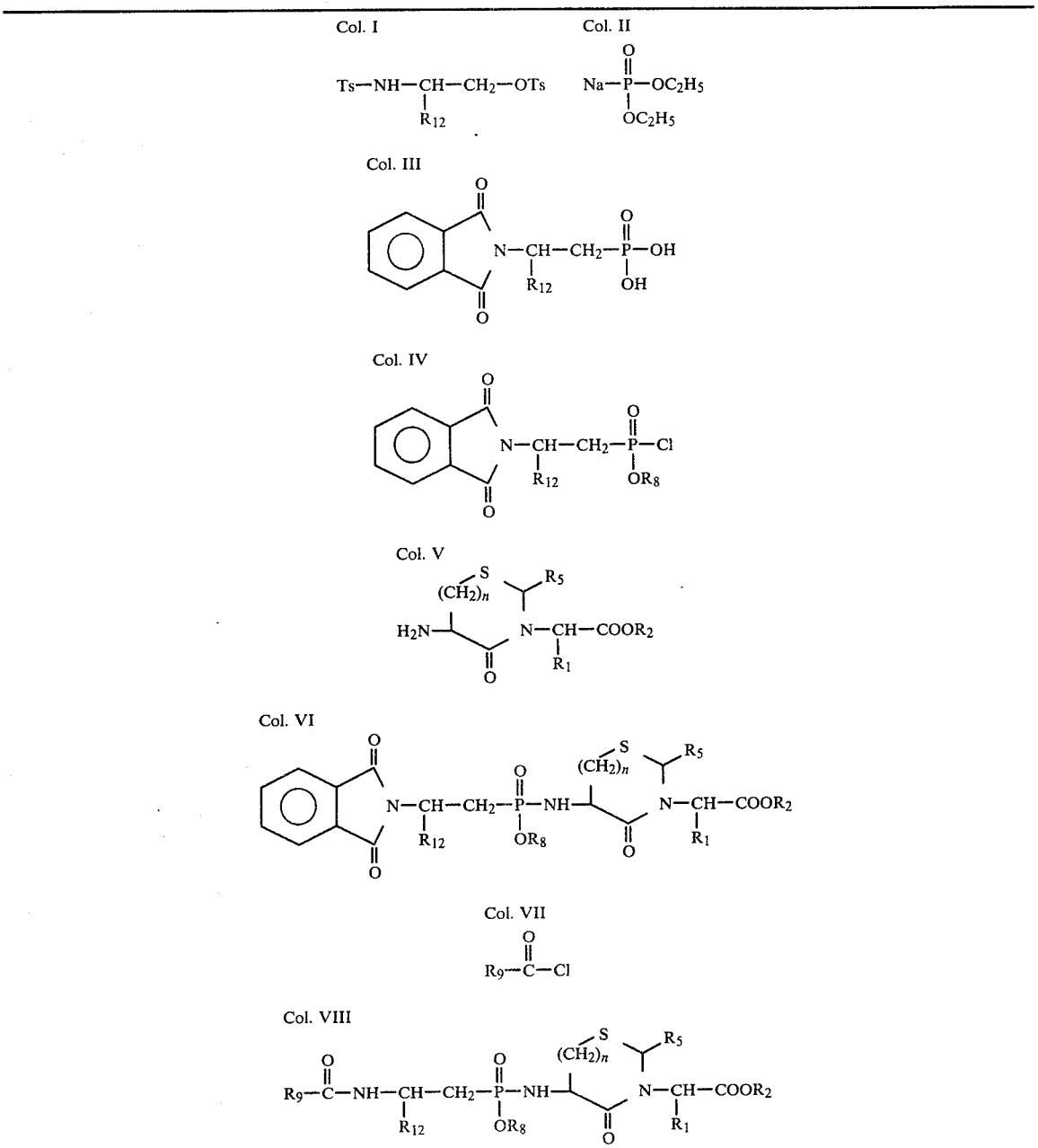

| Example | $R_{12}$ | $R_8$ | n | $R_5$ | $R_1$ | $R_2$ | $R_9$ |
|---|---|---|---|---|---|---|---|
| 36 | phenyl-(CH$_2$)$_2$— | —C$_2$H$_5$ | 2 | —H | —H | —C$_2$H$_5$ | phenyl- |
| 37 | thienyl-CH$_2$— | —C$_2$H$_5$ | 1 | —H | —H | —C$_2$H$_5$ | Cl-phenyl- |

-continued
Col. I
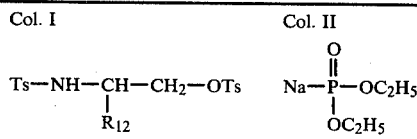
Col. II
Col. III
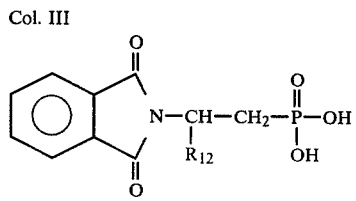
Col. IV
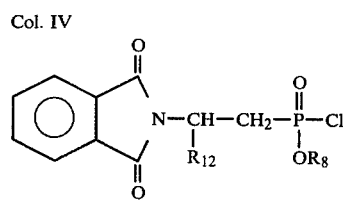
Col. V
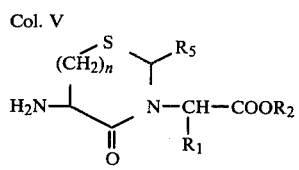
Col. VI
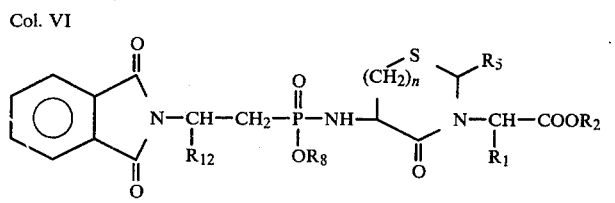
Col. VII
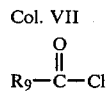
Col. VIII
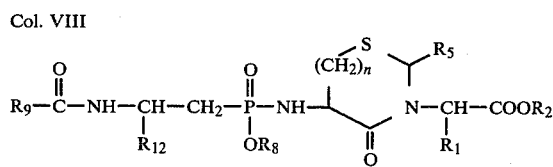
| Example | $R_{12}$ | $R_8$ | n | $R_5$ | $R_1$ | $R_2$ | $R_9$ |
|---|---|---|---|---|---|---|---|
| 38 | furan-CH₂CH₂— | $-C_2H_5$ | 2 | phenyl | $-CH_3$ | $-C_2H_5$ | phenyl-CH₂— |
| 39 | phenyl-CH₂— | $-C_2H_5$ | 1 | $-CH_3$ | $-H$ | $-C_2H_5$ | $H_3C-(CH_2)_3-$ |
| 40 | phenyl- | $-C_2H_5$ | 2 | $-C_2H_5$ | $-(CH_2)_4NHCOCH_2$-phenyl | $-C_2H_5$ | phenyl-$(CH_2)_2-$ |
| 41 | $(H_3C)_2HC-$ | $-C_2H_5$ | 1 | $-CH_2$-cyclohexyl | $-H$ | $-C_2H_5$ | thienyl-CH₂— |

-continued
Col. I
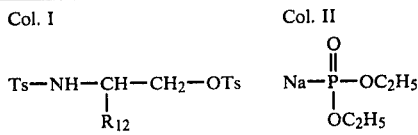
Col. II
Col. III
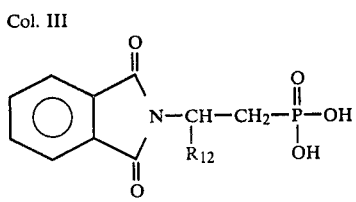
Col. IV
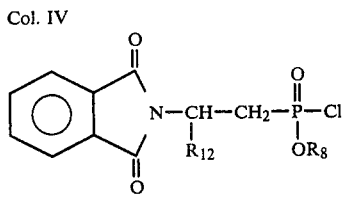
Col. V
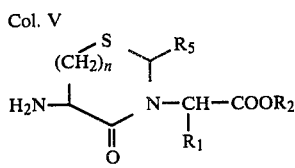
Col. VI
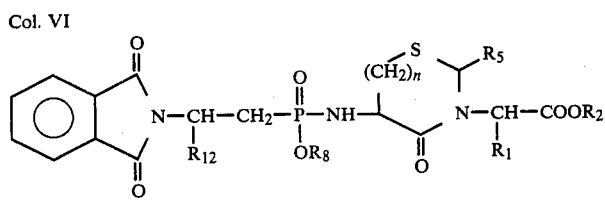
Col. VII
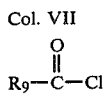
Col. VIII
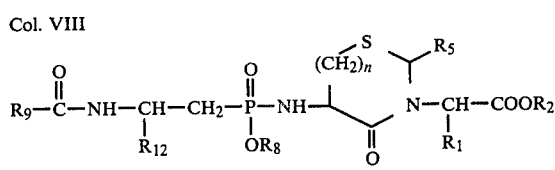
| Example | $R_{12}$ | $R_8$ | n | $R_5$ | $R_1$ | $R_2$ | $R_9$ |
|---|---|---|---|---|---|---|---|
| 42 | cyclohexyl-CH$_2$— | —C$_2$H$_5$ | 2 | 4-methylphenyl | —CF$_3$ | —C$_2$H$_5$ | pyridyl-CH$_2$— |
| 43 | pyridyl-CH$_2$— | —C$_2$H$_5$ | 1 | —H | —H | —C$_2$H$_5$ | phenyl-CH$_2$— |
| 44 | phenyl-CH$_2$— | —C$_2$H$_5$ | 2 | phenyl | —CH$_3$ | —C$_2$H$_5$ | cyclohexyl- |

-continued
Col. I
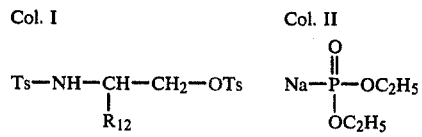
Col. II
Col. III
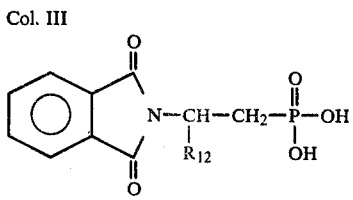
Col. IV
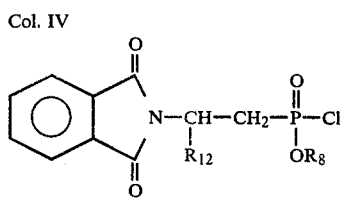
Col. V
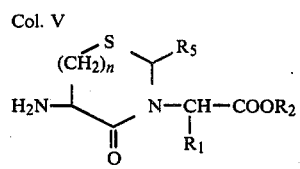
Col. VI
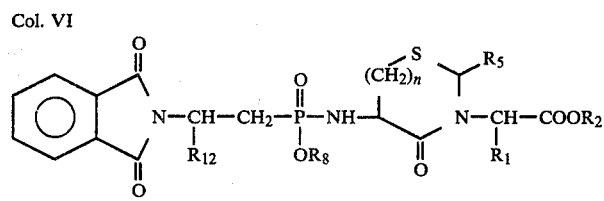
Col. VII
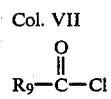
Col. VIII
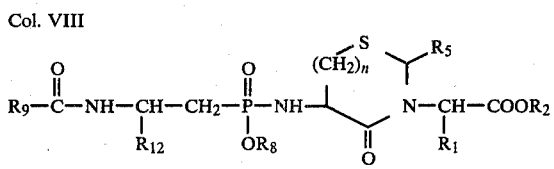
| Example | R₁₂ | R₈ | n | R₅ | R₁ | R₂ | R₉ |
|---|---|---|---|---|---|---|---|
| 45 | ⟨○⟩—CH₂— | —C₂H₅ | 1 | ⟨○⟩ | —H | —CH(CH(CH₃)₂)—O—C(O)—C₂H₅ | ⟨○⟩— |
Similarly, by employing the thiazine esters of Examples 17 to 29 within the procedure of Examples 35 to 45, other compounds within the scope of the invention are obtained.
EXAMPLE 46

(R)-Dihydro-5-[[1-(ethoxycarbonyl)-3-phenylpropyl]amino]-4-oxo-2-phenyl-2H-1,3-thiazine-3(4H)-acetic acid (a)
(R)-Dihydro-5-phthalimido-4-oxo-2-phenyl-2H-1,3-thiazine-3(4H)-acetic acid, ethyl ester (isomer A) and (isomer B)

The diastereomeric mixture of (R)-dihydro-5-phthalimido-4-oxo-2-phenyl-2H-1,3-thiazine-3(4H)-acetic acid, ethyl ester (15.6 g.) from Example 1(c) is refluxed in ether (500 ml.) for 4 hours, then cooled in an ice-bath and filtered to give 5.9 g. of isomer A at least 90% free of isomer B; m.p. 166°–168°. $[\alpha]_D = -72.9°$ (c=1, chloroform). TLC (hexane/ethyl acetate; 1:1) shows spot at $R_f = 0.40$.

Anal. Calcd. for $C_{22}H_{20}O_5N_2S$: C, 62.25; H, 4.75; N, 6.60; S, 7.55. Found: C, 62.21; H, 4.82; N, 6.63; S, 7.52.

A second, lower melting sample of isomer A (0.9 g., m.p. 162°–164°) is obtained by refluxing the remaining mixture in 125 ml. of ether and collecting the solid product. The remaining mixture (8 g.) is refluxed in 50 ml. of ether affording 250 mg. of insoluble material and 7.1 g. of soluble product enriched in isomer B. 5.8 g. of this material is purified chromatographically on two Waters Prep LC columns run with hexane:ethyl acetate (3:1). By this route, 4.8 g. of isomer B is obtained; m.p. 66°–68°; $[\alpha]_D = -101.2°$ (c=1, chloroform). TLC same as for isomer A.

Anal. Calcd. for $C_{22}H_{20}O_5N_2S \cdot 0.2H_2O$: C, 61.83; H, 4.79; N, 6.55; S, 7.50. Found: C, 61.83; H, 5.07; N, 6.25; S, 7.42.

(b)
(R)-Dihydro-5-phthalimido-4-oxo-2-phenyl-2H-1,3-thiazine-3(4H)-acetic acid, 2-(trimethylsilyl)ethyl ester (R)-Dihydro-5-phthalimido-4-oxo-2-phenyl-2H-1,3-thiazine-3(4H)-acetic acid, ethyl ester (isomer A) (1.0 g., 2.36 mmole) is heated in 2-trimethylsilylethanol (5.58 g., 47.2 mmole) in the presence of titanium (IV) ethoxide (135 mg., 0.59 mmole). Upon completion of the reaction, the reaction mixture is diluted with ether, washed with 1N hydrochloric acid, water, saturated aqueous sodium bicarbonate, and brine, dried ($MgSO_4$), and concentrated in vacuo. The residue is purified chromatographically on silica gel eluting with hexane/ethyl acetate (3:1) to give (R)-dihydro-5-phthalimido-4-oxo-2-phenyl-2H-1,3-thiazine-3(4H)-acetic acid, 2-(trimethylsilyl)ethyl ester.

(c)
(R)-Dihydro-5-amino-4-oxo-2-phenyl-2H-1,3-thiazine-3(4H)-acetic acid, 2-(trimethylsilyl)ethyl ester A solution of the trimethylsilyl ester product from part (b) (1.17 g., 2.36 mmole) in 4 ml. of dry chloroform is treated with N-methylhydrazine (217 mg., 4.72 mmole). The stoppered reaction is stirred at room temperature overnight, then diluted with ether and filtered to remove N-methyl-phthalhydrazide. Removal of organic solvents in vacuo yields (R)-dihydro-5-amino-4-oxo-2-phenyl-2H-1,3-thiazine-3(4H)-acetic acid, 2-(trimethylsilyl)ethyl ester.

(d)
(R)-Dihydro-5-[[1-(ethoxycarbonyl)-3-phenylpropyl]amino]-4-oxo-2-phenyl-2H-1,3-thiazine-3(4H)-acetic acid, 2-(trimethylsilyl)ethyl ester A solution of (R)-dihydro-5-amino-4-oxo-2-phenyl-2H-1,3-thiazine-3(4H)-acetic acid, 2-(trimethylsilyl)ethyl ester (9 mmole) in dry isopropanol (12 ml.) under nitrogen is treated with sodium bicarbonate (2.25 mmole) followed by ethyl-2-oxo-4-phenylbutyrate (9.3 g., 45 mmole) dissolved in isopropanol (8 ml.). To the resulting suspension is added powdered 3 A° molecular sieves (8 g.). The reaction mixture is stirred for one hour while the pH is maintained at around 7.0. Next a solution of sodium cyanoborohydride (1.13 g., 18 mmole) in isopropanol (14 ml.) is added incrementally over a 5 hour period while continuing to maintain neutral pH. The reaction mixture is then stirred overnight at room temperature, then filtered (celite), concentrated in vacuo, and partitioned between ether and water. Normal work up of the organic extract followed by column chromatography on silica gel yields (R)-dihydro-5-[[1-(ethoxycarbonyl)-3-phenylpropyl]amino]-4-oxo-2-phenyl-2H-1,3-thiazine-3(4H)-acetic acid, 2-(trimethylsilyl)ethyl ester as a mixture of diastereomers.

(e)
(R)-Dihydro-5-[[1-(ethoxycarbonyl)-3-phenylpropyl]amino]-4-oxo-2-phenyl-2H-1,3-thiazine-3(4H)-acetic acid A solution of (R)-dihydro-5-[[1-(ethoxycarbonyl)-3-phenylpropyl]amino]-4-oxo-2-phenyl-2H-1,3-thiazine-3(4H)-acetic acid, 2-(trimethylsilyl) ethyl ester (1.47 mmole) in dry dimethylformamide (4.5 ml.) is cooled in an ice-bath and reacted with a solution of n-tetrabutylammonium fluoride trihydrate (0.928 g., 2.94 mmole) in dimethylformamide (1.5 ml.). Upon disappearance of starting material, the reaction mixture is diluted with ethyl acetate (200 ml.) and washed with water (30 ml., twice). Normal work-up of the organic extract followed by chromatography affords (R)-dihydro-5-[[1-(ethoxycarbonyl)-3-phenylpropyl]amino]-4-oxo-2-phenyl-2H-1,3-thiazine-3(4H)-acetic acid as a mixture of diastereomers.

Similarly, the diastereomic mixture of (R)-dihydro-5-phthalimido-4-oxo-2-phenyl-2H-1,3-thiazine-3(4H)-acetic acid, ethyl ester or its isomer B could be employed in place of isomer A in the above procedure to yield other compounds within the scope of the invention.

EXAMPLE 47

(R)-Dihydro-5-[[1-carboxy-3-phenylpropyl]amino]-4-oxo-2-phenyl-2H-1,3-thiazine-3(4H)-acetic acid, dilithium salt A solution of (R)-dihydro-5-[[1-(ethoxycarbonyl)-3-phenylpropyl]amino]-4-oxo-2-phenyl-2H-1,3-thiazine-3(4H)-acetic acid (1 mmole), prepared as set forth in Example 46, in methanol (4 ml.) is treated with 1N aqueous lithium hydroxide (2 ml.). Upon completion of the reaction, the aqueous solution is filtered and chromatographed on an HP-20 (200 ml.) column eluting with a linear gradient of water-acetonitrile (10→90% acetonitrile). The desired fractions are combined, evaporated to a small volume, filtered (millipore) and lyophilized to give (R)-dihydro-5-[[1-carboxy-3-phenylpropyl]amino]-4-oxo-2-phenyl-2H-1,3-thiazine-3(4H)-acetic acid, dilithium salt.

EXAMPLES 48–70

Following the procedure of Example 46 but employing the keto compound shown in Col. I and the thiazine ester shown in Col. II, one obtains the product shown in Col. III. The $R_3$ and $R_4$ protecting groups shown in Examples 59, 61, and 63 to 65 are removed as the last step of the synthesis. The $R_2$ and $R_3$ ester groups can be removed to give the corresponding diacid which can then be converted to a salt. When it is desired to remove only the $R_2$ ester group and leave the $R_3$ ester group in place, then the thiazine ethyl ester is converted to its trimethylsilylethyl ester prior to reaction with the keto compound.

| Example | $R_3$ | $R_4$ | n | $R_5$ | $R_1$ | $R_2$ |
|---|---|---|---|---|---|---|
| 48 | —OC$_2$H$_5$ | —(CH$_2$)$_2$—C$_6$H$_5$ | 2 | —C$_6$H$_5$ | —CH$_3$ | —C$_2$H$_5$ |
| 49 | —OC$_2$H$_5$ | —CH$_2$—C$_6$H$_5$ | 1 | —H | —H | —C$_2$H$_5$ |
| 50 | —OC$_2$H$_5$ | —CH$_2$—O—C$_6$H$_5$ | 2 | —H | —H | —C$_2$H$_5$ |
| 51 | —OC$_2$H$_5$ | —CH$_2$—C$_6$H$_4$—OCH$_3$ | 1 | —CH$_3$ | —H | —C$_2$H$_5$ |
| 52 | —OH | —CH$_3$ | 2 | —H | —H | —C$_2$H$_5$ |
| 53 | —OCH$_2$N(CH$_3$)$_2$ | —CH$_2$—C$_6$H$_5$ | 1 | —C$_6$H$_5$ | —CF$_3$ | —C$_2$H$_5$ |
| 54 | —OCH$_2$NHCOCH$_3$ | —(CH$_2$)$_2$—C$_6$H$_5$ | 2 | —C$_6$H$_5$ | —H | —C$_2$H$_5$ |
| 55 | —O—CH$_2$—C$_6$H$_5$ | —CH(CH$_3$)$_2$ | 1 | —C$_6$H$_{11}$ | —H | —C$_2$H$_5$ |
| 56 | —NH—COCH$_2$—C$_6$H$_5$ | —CH$_2$—C$_6$H$_5$ | 2 | —H | —H | —C$_2$H$_5$ |
| 57 | —NH—C$_2$H$_5$ | —(CH$_2$)$_3$—C$_6$H$_5$ | 1 | —CH$_2$—C$_6$H$_5$ | —H | —C$_2$H$_5$ |
| 58 | —N(CH$_3$)$_2$ | —C$_2$H$_5$ | 2 | —C(CH$_3$)$_3$ | —H | —C$_2$H$_5$ |

-continued

| | Col. I | Col. II | | Col. III | | |
|---|---|---|---|---|---|---|
| Example | $R_3$ | $R_4$ | n | $R_5$ | $R_1$ | $R_2$ |
| 59 | —NH—CH$_2$—C$_6$H$_5$ | —CH$_2$—C$_6$H$_5$ | 1 | —H | —H | —C$_2$H$_5$ |
| 60 | —OC$_2$H$_5$ | —(CH$_2$)$_2$—cyclohexyl | 2 | —H | —C$_2$H$_5$ | —C$_2$H$_5$ |
| 61 | —OC$_2$H$_5$ | —CH$_2$—O—CH$_2$—C$_6$H$_5$ | 1 | —C$_6$H$_5$ | —H | —C$_2$H$_5$ |
| 62 | —OC$_2$H$_5$ | —(CH$_3$)$_2$SCH$_3$ | 2 | —C$_2$H$_5$ | —H | —C$_2$H$_5$ |
| 63 | —OC$_2$H$_5$ | —(CH$_2$)$_3$NHC(=NH)NH—NO$_2$ | 1 | —C$_6$H$_5$ | —H | —C$_2$H$_5$ |
| 64 | —OC$_2$H$_5$ | —(CH$_2$)$_4$NHC(=O)CH$_2$—C$_6$H$_5$ | 1 | —H | —H | —C$_2$H$_5$ |
| 65 | —OH | —CH$_2$-(1-benzylimidazol-4-yl) | 2 | —H | —H | —C$_2$H$_5$ |
| 66 | —OC$_2$H$_5$ | —CH$_2$-(indol-3-yl) | 1 | —C$_6$H$_5$ | —H | —C$_2$H$_5$ |
| 67 | —OC$_2$H$_5$ | —CH(CH$_2$C$_6$H$_5$)(NHC(=O)C$_6$H$_5$) | 1 | —C$_6$H$_5$ | —H | —C$_2$H$_5$ |
| 68 | —OC$_2$H$_5$ | —CH(CH$_2$C$_6$H$_5$)(NHC(=O)C$_6$H$_5$) | 2 | —H | —H | —C$_2$H$_5$ |

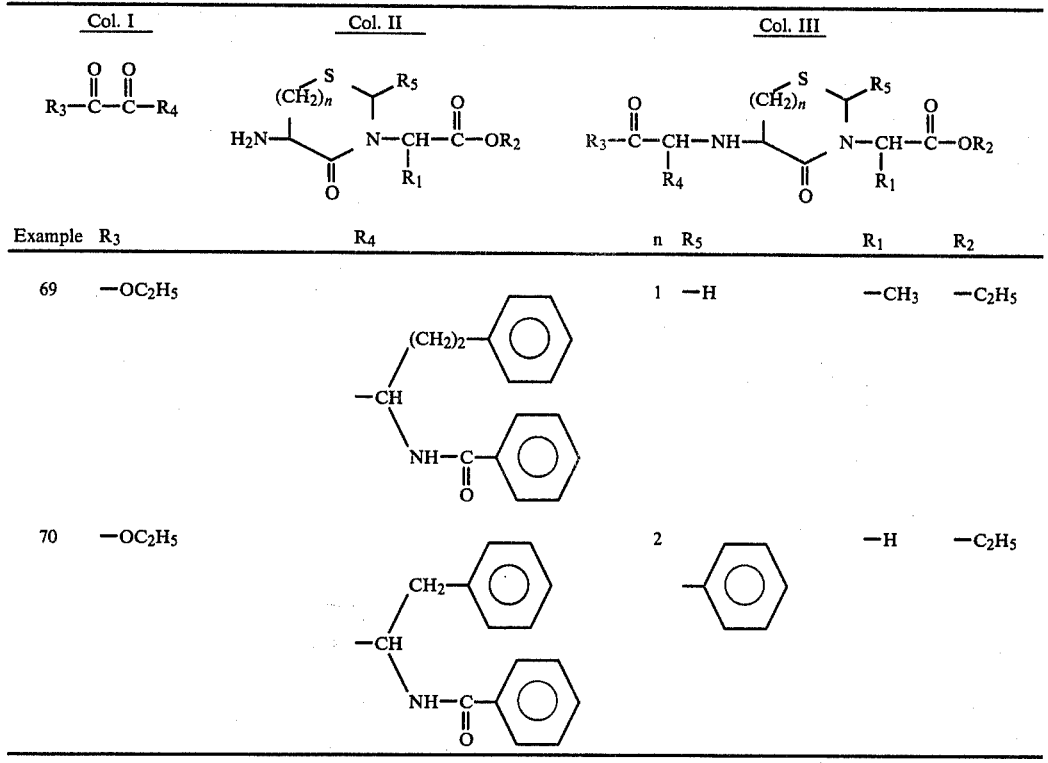

Similarly, by employing the thiazine esters of Examples 17 to 29 within the procedure of Examples 46 to 70, other compounds within the scope of the invention are obtained.

EXAMPLE 71

(R)-Dihydro-5-[[[2-methyl-1-(1-oxopropoxy)propoxy](4-phenylbutyl)phosphinyl]amino]-4-oxo-2-phenyl-2H-1,3-thiazine-3(4H)-acetic acid, monolithium salt (a)
(R)-Dihydro-5-phthalimido-4-oxo-2-phenyl-2H-1,3-thiazine-3(4H)-acetic acid, trimethylsilylethyl ester (R)-Dihydro-5-phthalimido-4-oxo-2-phenyl-2H-1,3-thiazine-3(4H)-acetic acid, ethyl ester is heated in trimethylsilylethanol in the presence of titanium (IV) ethoxide. Upon completion of the reaction, the reaction mixture is diluted with ether, washed with 1N hydrochloric acid, water, saturated aqueous sodium bicarbonate, and brine, dried (MgSO$_4$), and concentrated in vacuo. The residue is purified chromatographically on silica gel to yield (R)-dihydro-5-phthalimido-4-oxo-2-phenyl-2H-1,3-thiazine-3(4H)-acetic acid, trimethylsilylethyl ester.

(b)
(R)-Dihydro-5-amino-4-oxo-2-phenyl-2H-1,3-thiazine-3(4H)-acetic acid, trimethylsilylethyl ester A solution of the trimethylsilylethyl ester product from part (a) in dry chloroform is treated with N-methylhydrazine according to the procedure of Example 1(d) to give (R)-dihydro-5-amino-4-oxo-2-phenyl-2H-1,3-thiazine-3(4H)-acetic acid, trimethylsilylethyl ester.

(c)
(R)-Dihydro-5-[[ethoxy(4-phenylbutyl)phosphinyl]amino]-4-oxo-2-phenyl-2H-1,3-thiazine-3(4H)-acetic acid, trimethylsilylethyl ester Chloro(4-phenylbutyl)phosphinic acid, ethyl ester is reacted with (R)-dihydro-5-amino-4-oxo-2-phenyl-2H-1,3-thiazine-3(4H)-acetic acid, trimethylsilylethyl ester according to the procedure of Example 1(f) to yield (R)-dihydro-5-[[ethoxy(4-phenylbutyl)phosphinyl]amino]-4-oxo-2-phenyl-2H-1,3-thiazine-3(4H)-acetic acid, trimethylsilylethyl ester.

(d)
(R)-Dihydro-5-[[[2-methyl-1-(1-oxopropoxy)propoxy](4-phenylbutyl)phosphinyl]amino]-4-oxo-2-phenyl-2H-1,3-thiazine-3(4H)-acetic acid, trimethylsilylethyl ester A mixture of the diester product from part (c) and bis(trimethylsilyl)acetamide in methylene chloride is stirred at ambient temperature for several hours. After concentration in vacuo at 30°, methylene chloride is added followed by bromotrimethylsilane. The mixture is stirred at room temperature for several hours and concentrated in vacuo overnight. The residue is dissolved in methylene chloride and treated with triethylamine and water and again concentrated in vacuo. The residue is taken up in chloroform and treated with triethylamine, 1-chloroisobutyl propanoate, sodium chloride, and tetrabutylammonium iodide. The mixture is stirred at reflux temperature overnight. The reaction mixture is then concentrated in vacuo and ether is added to the residue. The water soluble solids separating from solution are filtered off and the ethereal filtrate is washed with water, 2% sodium thiosulfate, and brine, dried (MgSO$_4$), and concentrated in vacuo to give (R)-dihydro-5-[[[2-methyl-1-(1-oxopropoxy)propoxy](4- phenylbutyl)phosphinyl]amino]-4-oxo-2-phenyl-2H-1,3-thiazine-3(4H)-acetic acid, trimethylsilylethyl ester.

(e)

(R)-Dihydro-5-[[[2-methyl-1-(1-oxopropoxy)propoxy](4-phenylbutyl)phosphinyl]amino]-4-oxo-2-phenyl-2H-1,3-thiazine-3(4H)-acetic acid, monolithium salt The diester product from part (d) in dry dimethylformamide is treated with a solution of n-tetrabutylammonium fluoride in dimethylformamide. Upon disappearance of the starting material, the reaction mixture is diluted with ethyl acetate, washed with water, and concentrated in vacuo. The residue is dissolved in water and applied to an AG50×8(Li+) column eluting with water. Fractions containing the desired product are combined and lyophilized. The lyophilate is chromatographed on an HP-20 column eluting with a linear gradient of acetonitrile/water (0→90%). Fractions containing the desired product are combined, concentrated in vacuo and the residue is dissolved in water, filtered, and lyophilized to give (R)-dihydro-5-[[[2-methyl-1-(1-oxopropoxy)propoxy]-(4-phenylbutyl)phosphinyl]amino]-4-oxo-2-phenyl-2H-1,3-thiazine-3(4H)-acetic acid, monolithium salt.

EXAMPLES 72-77

Following the procedure of Example 71 but substituting for the 1-chloroisobutyl propanoate the alkylating agents listed below in Col. I, the products listed in Col. II are obtained.

Similarly, the alkylating agents of Examples 71 to 77 can be employed with the ester products of Examples 2 to 45 to yield other compounds within the scope of this invention.

EXAMPLE 78

(R)-Dihydro-5-[[hydroxy(4-phenylbutyl)phosphinyl]amino]-4-oxo-2-phenyl-2H-1,3-thiazine-3(4H)-acetic acid, disodium salt Following the procedure of Example 1 but substituting sodium hydroxide for the lithium hydroxide in part (g), one obtains (R)-dihydro-5-[[hydroxy(4-phenylbutyl)phosphinyl]amino]-4-oxo-2-phenyl-2H-1,3-thiazine-3(4H)-acetic acid, disodium salt.

This procedure can be employed in Examples 2–77 to give the corresponding mono or disodium salt. In a similar manner, the corresponding mono or dipotassium salt can be obtained.

EXAMPLE 79

1000 tablets each containing the following ingredients:

| | |
|---|---|
| (R)—Dihydro-5-[[hydroxy(4-phenylbutyl)phosphinyl]amino]-4-oxo-2-phenyl-2H—1,3-thiazine-3(4H)—acetic acid, disodium salt | 100 mg. |
| Corn starch | 50 mg. |
| Gelatin | 7.5 mg. |
| Avicel(microcrystalline cellulose) | 25 mg. |

| Example | Col. I | Col. II |
|---|---|---|
| 72 | Cl—CH(cyclohexyl)—O—C(=O)—C$_2$H$_5$ | (R)-Dihydro-5-[[[cyclohexyl(1-oxopropoxy)methoxy](4-phenylbutyl)phosphinyl]-amino]-4-oxo-2-phenyl-2H—1,3-thiazine-3(4H)-acetic acid, monolithium salt |
| 73 | Cl—CH(CH$_3$)—O—C(=O)—C$_2$H$_5$ | (R)-Dihydro-5-[[[1-(1-oxopropoxy)ethoxy](4-phenylbutyl)phosphinyl]amino]-4-oxo-2-phenyl-2H—1,3-thiazine-3(4H)-acetic acid, monolithium salt |
| 74 | Cl—CH$_2$—O—C(=O)—C(CH$_3$)$_3$ | (R)-Dihydro-5-[[[(2,2-dimethyl-1-oxopropoxy)methoxy]-(4-phenylbutyl)phosphinyl]-amino]-4-oxo-2-phenyl-2H—1,3-thiazine-3(4H)-acetic acid, monolithium salt |
| 75 | Cl—CH(CH(CH$_3$)$_2$)—O—C(=O)—(CH$_2$)$_2$—CH$_3$ | (R)-Dihydro-5-[[[2-methyl-1-(1-oxobutoxy)propoxy](4-phenylbutyl)phosphinyl]-amino]-4-oxo-2-phenyl-2H—1,3-thiazine-3(4H)-acetic acid, monolithium salt |
| 76 | Cl—CH$_2$—O—C(=O)—C$_6$H$_5$ | (R)-Dihydro-5-[[[(phenylcarbonyloxy)methoxy](4-phenylbutyl)phosphinyl]-amino]-4-oxo-2-phenyl-2H—1,3-thiazine-3(4H)-acetic acid, monolithium salt |
| 77 | Cl—CH$_2$—O—C(=O)—OC$_2$H$_5$ | (R)-Dihydro-5-[[[(ethoxycarbonyloxy)methoxy](4-phenylbutyl)phosphinyl]-amino]-4-oxo-2-phenyl-2H—1,3-thiazine-3(4H)-acetic acid, monolithium salt |

| | |
|---|---|
| Magnesium stearate | 2.5 mg. |
| | 185 mg. | are prepared from sufficient bulk quantities by mixing the (R)-dihydro-5-[[hydroxy(4-phenylbutyl)phosphinyl]amino]-4-oxo-2-phenyl-2H-1,3-thiazine-3(4H)-acetic acid, disodium salt and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 2 to 77 can be prepared.

EXAMPLE 80

1000 tablets each containing the following ingredients:

| | |
|---|---|
| Tetrahydro-6-[[hydroxy(4-phenylbutyl)phosphinyl]amino]-5-oxo-1,4-thiazepine-4(5H)—acetic acid, disodium salt | 50 mg. |
| Lactose | 25 mg. |
| Avicel | 38 mg. |
| Corn starch | 15 mg. |
| Magnesium stearate | 2 mg. |
| | 130 mg. | are prepared from sufficient bulk quantities by mixing the tetrahydro-6-[[hydroxy(4-phenylbutyl)phosphinyl]amino]-5-oxo-1,4-thiazepine-4(5H)-acetic acid, disodium salt, lactose and Avicel and then blending with the corn starch. Magnesium stearate is added and the dry mixture is compressed in a tablet press to form 1000 tablets each containing 50 mg. of active ingredient. The tablets are coated with a solution of Methocel E 15 (methyl cellulose) including as a color a lake containing yellow #6.

In a similar manner, tablets containing 50 mg. of the product of any Examples 1 to 16 and 18 to 78 can be prepared.

EXAMPLE 81

Two piece #1 gelatin capsules each containing 100 mg. of (R)-dihydro-5-[[1-(ethoxycarbonyl)-3-phenylpropyl]amino]-4-oxo-2-phenyl-2H-1,3-thiazine-acetic acid, monosodium salt are filled with a mixture of the following ingredients:

| | |
|---|---|
| (R)—Dihydro-5-[[1-(ethoxycarbony)-3-phenylpropyl]amino]-4-oxo-2-phenyl-2H—1,3-thiazine-acetic acid, monosodium salt | 100 mg. |
| Magnesium stearate | 7 mg. |
| Lactose | 193 mg. |
| | 300 mg. |

In a similar manner, capsules containing 100 mg. of the product of any of Examples 1 to 45 and 47 to 78 can be prepared.

EXAMPLE 82

An injectable solution is prepared as follows:

| | |
|---|---|
| (±)-Dihydro-3-[[hydroxy(4-phenylbutyl)phosphinyl]amino]-4-oxo-1,5-benzothiazepine-5(2H)—acetic acid, disodium salt | 500 g. |
| Methyl paraben | 5 g. |
| Propyl paraben | 1 g. |
| Sodium chloride | 25 g. |
| Water for injection | 5 l. |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any Examples 1 to 28 and 30 to 78.

EXAMPLE 83

1000 tablets each containing the following ingredients:

| | |
|---|---|
| (R)—Dihydro-5-[[hydroxy(4-phenylbutyl)phosphinyl]amino]-4-oxo-2-phenyl-2H—1,3-thiazine-3(4H)—acetic acid, disodium salt | 100 mg. |
| Avicel | 100 mg. |
| Hydrochlorothiazide | 12.5 mg. |
| Lactose | 113 mg. |
| Corn starch | 17.5 mg. |
| Stearic acid | 7 mg. |
| | 350 mg. | are prepared from sufficient bulk quantities by slugging the (R)-dihydro-5-[[hydroxy(4-phenylbutyl)phosphinyl]amino]-4-oxo-2-phenyl-2H-1,3-thiazine-3(4H)-acetic acid, disodium salt, Avicel and a portion of the stearic acid. The slugs are ground and passed through a #2 screen, then mixed with the hydrochlorothiazide, lactose, corn starch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 2 to 77.

What is claimed is:

1. A compound of the formula

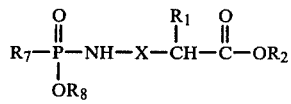

and pharmaceutically acceptable salts thereof wherein:

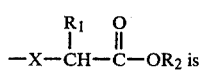 is

-continued

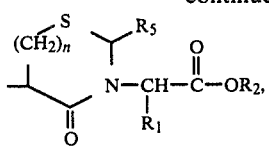

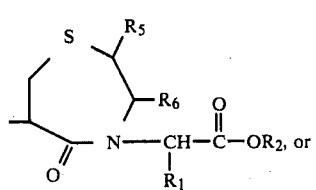

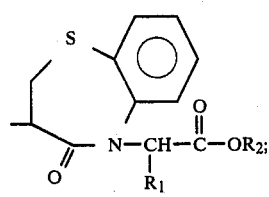

$R_1$ is hydrogen, lower alkyl, amino substituted lower alkyl, hydroxy substituted lower alkyl, or halo substituted lower alkyl;
n is one or two;
$R_5$ and $R_6$ are independently selected from the group consisting of hydrogen, lower alkyl, —$(CH_2)_m$-cycloalkyl wherein said cycloalkyl is a saturated ring of 3 to 7 carbons, and

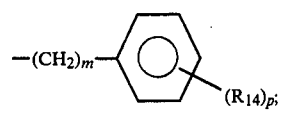

m is zero or an integer from 1 to 4;
$R_{14}$ is hydrogen, lower alkyl of 1 to 4 carbons, lower alkoxy of 1 to 4 carbons, lower alkylthio of 1 to 4 carbons, halo, trifluoromethyl, or hydroxy;
p is an integer from 1 to 3 provided that p is more than one only if $R_{14}$ is hydrogen, methyl, methoxy, chloro, or fluoro;
$R_7$ is alkyl of 1 to 10 carbons,

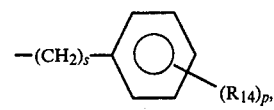

—$(CH_2)_s$-cycloalkyl wherein cycloalkyl is a saturated ring of 3 to 7 carbons, —$(CH_2)_t$—$NH_2$

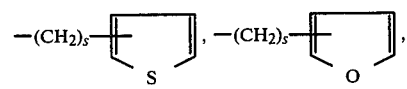

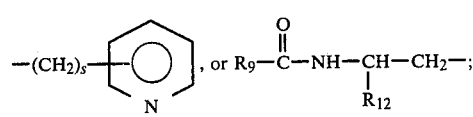

s is zero or an integer from 1 to 7;
t is an integer from 1 to 8;

$R_9$ and $R_{12}$ are independently selected from the group consisting of lower alkyl, halo substituted lower alkyl-$(CH_2)_m$-cycloalkyl wherein cycloalkyl is a saturated ring of 3 to 7 carbons,

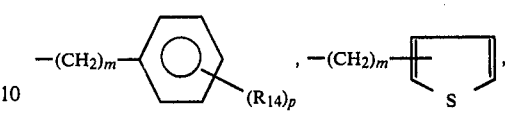

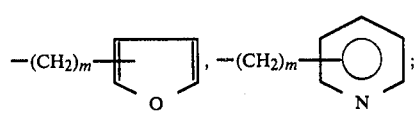

$R_8$ and $R_2$ are independently selected from the group consisting of hydrogen, lower alkyl, benzhydryl, an alkali metal ion, an alkaline earth metal ion, and

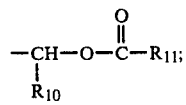

$R_{10}$ is hydrogen, lower alkyl, cycloalkyl wherein cycloalkyl is a saturated ring of 3 to 7 carbons or phenyl; and
$R_{11}$ is hydrogen, lower alkyl, lower alkoxy, cycloalkyl wherein cycloalkyl is a saturated ring of 3 to 7 carbons, phenyl, benzyl, or phenethyl.

2. A compound of claim 1 wherein:
$R_7$ is alkyl of 1 to 10 carbons,

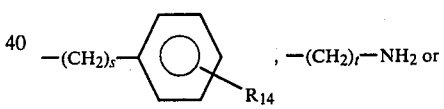

$R_9$ and $R_{12}$ are independently selected from the group consisting of lower alkyl of 1 to 4 carbons and

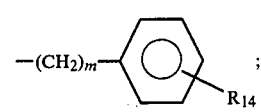

s is zero or an integer from 1 to 7;
t is an integer from 1 to 8;
m is zero, one, two or three;
$R_{14}$ is hydrogen, methyl, methoxy, methylthio, chloro, bromo, fluoro, or hydroxy;
$R_1$ is hydrogen, lower alkyl of 1 to 4 carbons, or —$(CH_2)_4$—$NH_2$;
$R_5$ and $R_6$ are independently selected from the group consisting of hydrogen, lower alkyl of 1 to 4 carbons and

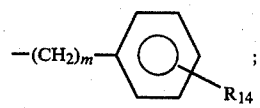

$R_8$ and $R_2$ are independently selected from the group consisting of hydrogen, lower alkyl of 1 to 4 carbons, alkali metal salt, and

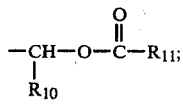

$R_{10}$ is hydrogen, straight or branched chain lower alkyl of 1 to 4 carbons, or cyclohexyl; and
$R_{11}$ is straight or branched chain lower alkyl of 1 to 4 carbons, cyclohexyl or phenyl.

3. A compound of claim 2 wherein:
$R_9$ is phenyl; and
$R_{12}$ is benzyl or phenethyl.

4. A compound of claim 2 wherein:

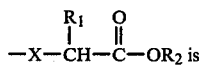

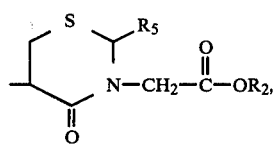

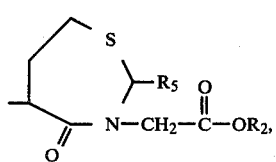

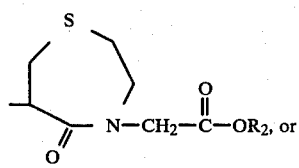

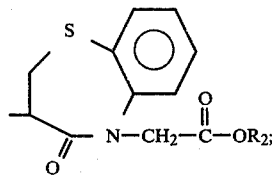

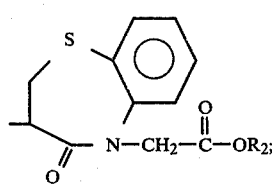

$R_7$ is alkyl of 1 to 10 carbons or

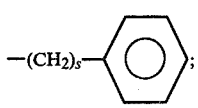

s is zero or an integer from 1 to 7;
$R_5$ is hydrogen or phenyl;
$R_8$ and $R_2$ are independently selected from the group consisting of hydrogen, alkali metal ion, and

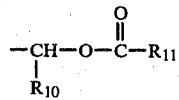

provided that only one of $R_2$ and $R_8$ is

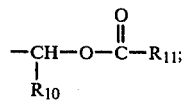

$R_{10}$ is hydrogen, straight or branched chain lower alkyl of 1 to 4 carbons, or cyclohexyl; and
$R_{11}$ is straight or branched chain lower alkyl of 1 to 4 carbons.

5. A compound of claim 4 wherein:

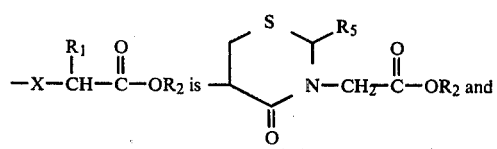

$R_5$ is hydrogen or phenyl.

6. A compound of claim 4 wherein:

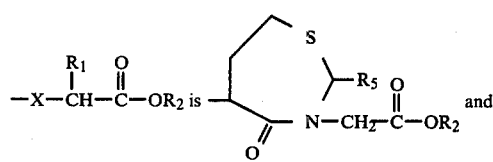

$R_5$ is hydrogen or phenyl.

7. A compound of claim 4 wherein:

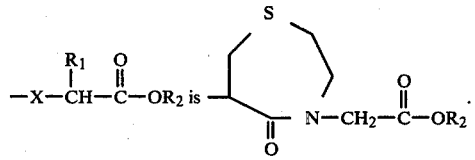

8. A compound of claim 4 wherein:

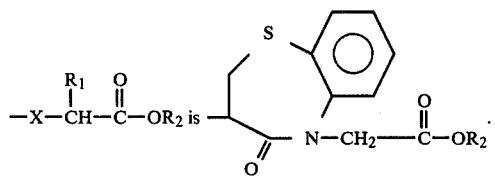

9. A compound of claim 5 wherein $R_5$ is phenyl.
10. A compound of claim 9 wherein:
$R_7$ is

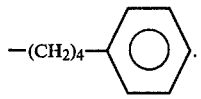

11. The compound of claim 10, (R)-dihydro-5-[[hydroxy(4-phenylbutyl)phosphinyl]amino]-4-oxo-2-phenyl-2H-1,3-thiazine-3(4H)-acetic acid, dilithium salt.

12. A compound of claim 6 wherein:
R₇ is

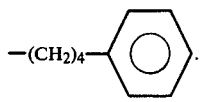

13. A compound of claim 7 wherein:
R₇ is

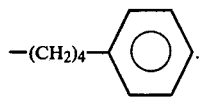

14. The compound of claim 13, tetrahydro-6-[[hydroxy(4-phenylbutyl)phosphinyl]amino]-5-oxo-1,4-thiazepine-4(5H)-acetic acid, dilithium salt.

15. A compound of claim 8 wherein:
R₇ is

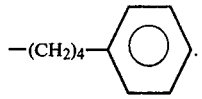

16. The compound of claim 15, (±)-dihydro-3-[[hydroxy(4-phenylbutyl)phosphinyl]amino]-4-oxo-1,5-benzothiazepine-5(2H)-acetic acid, dilithium salt.

17. A composition useful for treating hypertension comprising a pharmaceutically acceptable carrier and a hypotensively effective amount of a hypotensive agent or pharmaceutically acceptable salt thereof of the formula $$R_7-\overset{O}{\underset{R_8}{\overset{\|}{P}}}-NH-X-\overset{R_1}{\underset{}{\overset{|}{C}H}}-\overset{O}{\overset{\|}{C}}-OR_2$$

wherein R₇, R₈ and $$-X-\overset{R_1}{\underset{}{\overset{|}{C}H}}-\overset{O}{\overset{\|}{C}}-OR_2$$

are as defined in claim 1.

18. A method of treating hypertension in a mammalian specie which comprises administering a hypotensively effective amount of the composition of claim 17.

* * * * *

UNITED STATES PATENT AND TRADEMARK OFFICE
CERTIFICATE OF CORRECTION

PATENT NO. : 4,460,579
DATED : July 17, 1984
INVENTOR(S) : Donald S. Karanewsky

It is certified that error appears in the above-identified patent and that said Letters Patent are hereby corrected as shown below:

Column 3, line 32, delete "-$(CH_2)_s$-$NH_2$," and add
-- -$(CH_2)_t$-$NH_2$, --.
Column 32, line 55, delete "(R)-Dihydro-5-[[(2-" and add
-- (R)-Dihydro-5-[[[2- --.

Signed and Sealed this

Fifth Day of November 1985

[SEAL]

Attest:

Attesting Officer

DONALD J. QUIGG

Commissioner of Patents and Trademarks